US010818397B2

(12) United States Patent
Dejori

(10) Patent No.: US 10,818,397 B2
(45) Date of Patent: *Oct. 27, 2020

(54) CLINICAL CONTENT ANALYTICS ENGINE

(71) Applicant: Zynx Health Incorporated, Los Angeles, CA (US)

(72) Inventor: Mathaeus Dejori, Los Angeles, CA (US)

(73) Assignee: Zynx Health Incorporated, Los Angeles, CA (US)

( * ) Notice: Subject to any disclaimer, the term of this patent is extended or adjusted under 35 U.S.C. 154(b) by 282 days.

This patent is subject to a terminal disclaimer.

(21) Appl. No.: 16/002,558

(22) Filed: Jun. 7, 2018

(65) Prior Publication Data

US 2018/0293354 A1 Oct. 11, 2018

Related U.S. Application Data

(63) Continuation of application No. 14/183,919, filed on Feb. 19, 2014, now Pat. No. 9,996,670.

(Continued)

(51) Int. Cl.
*G16H 50/20* (2018.01)
*G06F 19/00* (2018.01)
*G16H 50/70* (2018.01)

(52) U.S. Cl.
CPC ............ *G16H 50/20* (2018.01); *G06F 19/00* (2013.01); *G16H 50/70* (2018.01)

(58) Field of Classification Search
CPC ........ G06N 20/00; G06N 3/08; G06N 3/0454; G06N 3/063; G06N 7/005; G06T 1/20;

(Continued)

(56) References Cited

U.S. PATENT DOCUMENTS

| 4,491,725 A | 1/1985 | Pritchard |
| 4,857,713 A | 8/1989 | Brown |

(Continued)

FOREIGN PATENT DOCUMENTS

| WO | WO 02/19221 | 3/2002 |
| WO | WO 03/030787 | 4/2003 |

(Continued)

OTHER PUBLICATIONS

U.S. Appl. No. 13/957,714, filed Aug. 2, 2013, Harp et al.

(Continued)

*Primary Examiner* — Maroun P Kanaan
(74) *Attorney, Agent, or Firm* — Knobbe, Martens, Olson & Bear LLP

(57) ABSTRACT

Clinical content analytics engines and associated processes are described. An engine receives a clinical decision support document, accesses corresponding reference content, identifies and extracts medical intervention content from the clinical decision support document, segments extracted medical intervention content into a first plurality of segments including at least a first segment comprising a first set of text, determines if the first segment corresponds to at least a first item included in the reference content, the first item comprising a second set of text comprising terminology different than that found in the first set of text, and in response to determining that the first segment corresponds to the first item included in the reference content, causing a report to include an indication that the first segment corresponds to the first item included in the reference content.

25 Claims, 16 Drawing Sheets

Related U.S. Application Data

(60) Provisional application No. 61/823,088, filed on May 14, 2013.

(58) Field of Classification Search
CPC ......... G06T 1/60; G06F 3/067; G06F 16/245; G06F 16/248; G06F 40/56; G06F 19/324; G06F 19/326; G06F 40/166; G06F 19/00; G06F 40/169; G06F 19/321; G06F 19/328; G06F 16/93; G06F 40/295; G06F 40/03; G06Q 10/10; G06Q 50/24; G06Q 10/06; G06Q 30/04; G06Q 40/08; G16H 15/00; G16H 10/20; G16H 40/63; G16H 10/60; G16H 50/20; G16H 50/70; G16H 30/40; G16H 70/00
See application file for complete search history.

(56) References Cited

U.S. PATENT DOCUMENTS

| | | |
|---|---|---|
| 5,664,109 A | 9/1997 | Johnson et al. |
| 5,786,816 A | 7/1998 | Macrae et al. |
| 6,018,713 A | 1/2000 | Coli et al. |
| 6,073,106 A | 6/2000 | Rozen et al. |
| 6,463,417 B1 | 10/2002 | Schoenberg |
| 6,694,334 B2 | 2/2004 | DuLong et al. |
| 7,822,626 B2 | 10/2010 | Harp et al. |
| 7,945,453 B2 | 5/2011 | Harp |
| 8,429,179 B1 | 4/2013 | Mirhaji |
| 8,504,381 B2 | 8/2013 | Harp et al. |
| 2001/0044731 A1 | 11/2001 | Coffman |
| 2002/0042726 A1 | 4/2002 | Mayaud |
| 2002/0059080 A1 | 5/2002 | Kasirer et al. |
| 2002/0095313 A1 | 7/2002 | Haq |
| 2004/0128165 A1 | 7/2004 | Block et al. |
| 2004/0153341 A1 | 8/2004 | Brandt |
| 2006/0149416 A1 | 7/2006 | Mohapatra et al. |
| 2007/0067183 A1 | 3/2007 | Harp |
| 2007/0067184 A1 | 3/2007 | Harp |
| 2007/0165625 A1 | 7/2007 | Eisner |
| 2007/0178501 A1 | 8/2007 | Rabinowitz |
| 2009/0254509 A1 | 10/2009 | Baluta |
| 2010/0004948 A1 | 1/2010 | Toomey |
| 2010/0250282 A1 | 9/2010 | Johnson |
| 2011/0145018 A1 | 6/2011 | Fotsch |
| 2011/0289403 A1 | 11/2011 | McDonald |
| 2011/0295873 A1 | 12/2011 | Potter |
| 2011/0301982 A1 | 12/2011 | Green, Jr. |
| 2013/0035961 A1 | 2/2013 | Yegnanarayanan |
| 2013/0054512 A1 | 2/2013 | Ephrat |
| 2013/0085781 A1 | 4/2013 | Navani |
| 2013/0085798 A1 | 4/2013 | Spatola |

FOREIGN PATENT DOCUMENTS

| | | |
|---|---|---|
| WO | WO 2006/060572 | 6/2006 |
| WO | WO 2014/018413 | 1/2014 |

OTHER PUBLICATIONS

Abstract for Anderson et al., "Physician Utilization of Computers in Medical Practice: Policy Implications based on a Structural Model," Social Science and Medicine, 1986, (1 pg.).

Abstract for Goldstein, Mary K., M.D., "Ontology-Based Physician Order Sets," prior to Aug. 25, 2006 (1 pg.).

Abstract for Groopman et al., "Effect of 'Standard Order' Deletion on Emergency Department Coagulation Profile Use," Annals of Emergency Medicine, 1992, (1 pg.).

Abstract for "Medical Test Results You Can View," Link-Up, Jul. 1, 2000, (1 pg.).

Abstract for Overhage et al., "A Randomized Trial of 'Corollary Orders' to Prevent Errors of Omission," J. Am. Med. Inform. Assoc., 1997, vol. 4, No. 5, (1 pg.).

Abstract for Schuster et al., "Involving Users in the Implementation of an Imaging Order Entry System," Journal of the American Medical Informatics Association, 2003, (1 pg.).

Fitzpatrick et al., If You Build It (Right) They Will Come: The Physician-Friendly CPOE: Not Everything Works as Planned Right Out of the Box. A Mississippi Hospital Customizes its Electronic Order Entry System for Maximum Use by Physicians (Computerized Physician Order Entry, Health Mgmt. Tech., Jan. 1, 2005, 26(1).

Franklin et al., "Modifiable Templates Facilitate Customization of Physician Order Entry," Proc. AMIA Symp., 1998, pp. 315-319, (6 pgs.).

Health Management Technology's If you build it (right) they will come: the physician-friendly CPOE: not everything works as planned right out of the box. A Mississippi hospital customizes its electronic order entry system for maximum use by physicians. (computerized physician order entry) (Aug. 15, 1989).

International Search Report and Written Opinion from PCT/US2013/051370 dated Oct. 29, 2013, 12 pages.

Pallato, John, "Health-Care Software Takes Care of Records, Helps Staff Plan Ahead," PC Week, Jul. 7, 1987, vol. 4, No. 27, p. 117 (1 pg.).

Payne, The transition to automated practitioner order entry in a teaching hospital: the VA Puget Sound experience, Proc AMIA Symp. 1999:589-593.

Samet et al., "Development and Implementation of a Multidisciplinary Review and Approval Process for Pre-Printed Physician Orders," ASHP Midyear Clinical Meeting, 2005, vol. 40, (2 pgs.).

Tjahjono et al., "Promoting the Online Use of Radiology Appropriateness Criteria," Radiographies, 1999, vol. 19, No. 6, pp. 1673-1681, (9 pgs.).

Wang, Xueyun Sharon, Nayda, Leonard, and Dettinger, Richard. "Infrastructure for a Clinical-Decision-Intelligence System." IBM Systems Journal 46, No. 1 (2007): pp. 151-169.

2012-CHF Dx-Specific          Patient Information:

Patient Care Orders

- ☑ CHF packet/teaching
- ☑ I&O
- ☑ Daily Weights
- ☑ Provide scale if appropriate
- ☑ EKG PRN, Place order when completed
- ☐ FSBS (Specify) AC and HS
- ☐ 2 or more FSBS > 150, convert to Glycemic Protocol

Laboratory

Cardiac Profile short order set

- CPK
  - ☐ Stat
- CKMB
  - ☐ Stat
- Troponin
  - ☐ Stat

FIG. 5A

2012-CHF Dx-Specific

CHF packet/teaching

☑ Education, self-management
☐ • 60 minutes of education by qualified educator, or • AHA Heart Failure interactive workbook provided
☐ Provide written discharge instructions or other educational material addressing all of the following* • Activity level • Diet • Discharge medications • Follow-up appointment • Weight monitoring • What to do if symptoms worsen
☐ Noninvasive positive pressure ventilation (For patients with acute cardiogenic pulmonary edema)
☐ ACE inhibitor*
☐ ARB*
☐ Aldosterone antagonist* (Prescribed at discharge for hospitalized patients)
☐ Beta-Blocker*
☐ Digoxin*
☐ Diuretic*
☐ HMG-CoA Reductase Inhibitor*
☐ HydrALAZINE + + isosorbide dinitrate (For African American patients)
☐ Pneumococcal immunization
☐ Assess left ventricular function
☐ Consult for cardiac resynchronization (For patients with LVEF < 35%, QRS interval >

[Save changes] [Close]

FIG. 5B

2012-CHF Dx-Specific     Patient Information:

Patient Care Orders

- ☑ CHF packet/teaching
- ☑ I&O
- ☑ Daily Weights
- ☑ Provide scale if appropriate
- ☑ EKG PRN, Place order when completed
- ☐ FSBS (Specify) AC and HS
- ☐ 2 or more FSBS > 150, convert to Glycemic Protocol

Laboratory

Cardiac Profile short order set
- ☐ CPK
  - Stat
- ☐ CKMB
  - Stat
-    Troponin

FIG. 5C

| Interventions | In Examined Content? | Section | Status | Assignee | Actions |
|---|---|---|---|---|---|
| 60 minutes of education or AHA workbook | No | PATIENT EDUCATION | Not Started | None | |
| Follow-up appointment within 48 hours | No | REMINDER | Not Started | None | |
| Pneumococcal immunization | No | MEDICATION | Sent to Zynx | jsmith@communityhospital.com | |
| Consult to cardiac rehabilitation | No | CONSULT | Not Started | None | |
| Consult for cardiac resynchronization | No | CONSULT | Not Started | None | |
| Consult for coronary angiography | No | CONSULT | Not Started | None | |
| Consult to discharge planning plus postdischarge follow-up care | No | CONSULT | Not Started | None | |
| Consult for implantable cardioverter-defibrillator | No | CONSULT | Not Started | None | |
| Education, self-management | No | PATIENT EDUCATION | Not Started | None | |
| HMG-CoA Reductase Inhibitor | No | MEDICATION | Not Started | None | |
| Noninvasive positive pressure ventilation | No | MEDICATION | Not Started | None | |

| | | | | | |
|---|---|---|---|---|---|
| ♀ Outcome Measures ▼ | ♀ Performance Measures ▼ | | | | Views ▼ |

Add export content and evidence links to your Tasks page. [View/Export Tasks]

| Interventions | In Examined Content? | Section | Status | Assignee | Actions |
|---|---|---|---|---|---|
| ☐ 60 minutes of education or AHA workbook | No | PATIENT EDUCATION | Not Started | None | ✉ ⊖ 🔲 ♀ |
| ☐ Follow-up appointment within 48 hours | No | REMINDER | Pending Research | jsmith@commun ityhospital.com | ⊖ 🏠 ♀ |
| ☐ Pneumococcal immunization | No | | | Remove or Override ⊖ | 🏢 ♀ |

| Details | ☑ Content | ☐ Notes |
|---|---|---|

Section: MEDICATION     Status: Sent to Zynx     Assignee: zynxvalue+@zynx.com

SUBPOPULATION
For patients 65 years of age and older who are at high risk for clinical deterioration or hospital admission.

EVIDENCE
① Pneumococcal immunization
1⊕ Add Evidence Link

OTHER ORGANIZATIONS LIKE YOU DO THIS
1⊕ 1⊕ 1⊕  Heart Failure Admission Orders

OUTCOME MEASURES
• Cost

PERFORMANCE MEASURES
(CMS ARRA 2) (CMS NHQM) (TJC NHQM)

Order Set: Heart Failure Admission Orders
Section Title: Medications Other
Line Item: IMMUNIZATIONS: Give pneumonia and flu vaccine according to hospital protocol.

CLINICAL CONTENT ANALYTICS ENGINE

Any and all applications for which a foreign or domestic priority claim is identified in the Application Data Sheet as filed with the present application, are hereby incorporated by reference in their entirety under 37 CFR 1.57.

BACKGROUND

Field of the Invention

The present invention is related to systems and methods for performing analytics, and in particular, on performing analytics on content, such as medical clinical decision support content.

Description of the Related Art

Conventionally, clinical decision support content used by medical care providers, such as hospitals and clinics, is often outdated and does not conform to recent related developments, such as FDA safety alerts, new findings, and new regulations. Thus, patients often do not receive treatment in accordance with the latest best practices.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

Certain example embodiments provide a system and process that analyze and assess content, such as clinical decision support (CDS) content, against reference content and identifies potential deficiencies. By way of example and not limitation, the reference content may comprise some or all of the following: clinical guidelines, clinical guidelines checklists, FDA checklists, FDA safety alerts, KCP data sources (Key Clinical Process, which may be a physical or electronic document or other data source that provides information regarding impacts to cost and outcomes of medical interventions as identified in medical literature), regulations, new findings, other changes to clinical evidence, other types of reference content, etc.

The system may identify where a CDS document is deficient relative to reference content and/or where the CDS document is consistent relative to the reference content, and may generate a report indicating such deficiencies and consistencies. The system optionally generates and reports update recommendations to be incorporated into the CDS document. Thus, the system may be used to better ensure that CDS content (e.g., order sets, care plans, clinical decision support rules, etc.), such as that of a hospital or other medical service provider, is current with new clinical guidelines and other reference content, and optionally is harmonized throughout a medical service provider's organization, resulting in better medical treatment outcomes for patients.

Optionally, the reports and/or recommendations may be generated and accessed by the service provider(s) in substantially real time. Optionally the reports and/or recommendations may be generated in a machine readable format (e.g., in a digital format, a QR code, other bar code, etc.) and transmitted to and processed by an EHR (Electronic Health Record) system and/or the reports and/or recommendations may be generated in a human readable format.

An example aspect provides a method of analyzing a clinical decision support (CDS) document, the method comprising: receiving at a computer system, including hardware and comprising an analytics engine, a clinical decision support document and/or data extract from a medical service provider system; accessing, by the computer system, reference content corresponding at least in part to the clinical decision document (optionally, appropriate reference content may be accessed manually and/or automatically); using the computer system, identifying and extracting medical intervention content from the clinical decision support document; segmenting, by the computer system, at least a portion of the extracted medical intervention content into a first plurality of segments including at least a first segment, comprising a first set of text, and a second segment comprising a second set of text; determining, by the computer system, if the first segment corresponds to at least a first item included in the reference content, the first item comprising a third set of text comprising terminology not present in the first and second sets of text; at least partly in response to determining that the first segment, comprising the first set of text, corresponds to the first item included in the reference content, the first item comprising the third set of text, causing a version of the clinical decision document to include an indication that the first segment corresponds to the first item included in the reference content; determining if a second item included in the reference content corresponds to at least one of the first plurality of segments; at least partly in response to determining that the second item included in the reference content does not correspond to at least one of the first plurality of segments, causing the version of the clinical decision document to include an indication that the first plurality of segments fails to include at least one segment that corresponds to the second item included in the reference content. The foregoing example method may optionally include only a subset of the foregoing actions.

The foregoing example method may optionally further comprise one or more of the following: the clinical decision support document comprises at least one of an order set, a care plan, or clinical support rules; the reference content comprises a clinical guideline or a checklist, or both a clinical guideline and a checklist; determining if the first segment corresponds to the first item included in the reference content further comprises determining if the first segment comprises a functional synonym using different terminology with respect to the first item included in the reference content; the clinical decision support document comprises field identifiers and corresponding data; determining whether a first character string in the clinical decision support document corresponds to a network protocol and at least partly in response to determining that the first character string in the clinical decision support document corresponds to a network protocol, excluding the first character string from the first plurality of segments; determining whether a first character string in the clinical decision support document exceeds a first number of words or characters and at least partly in response to determining that the first character string in the clinical decision support document exceeds the first number of words or characters, excluding the first character string from the first plurality of segments; wherein segmenting, by the computer system, at least a portion of the extracted content into the first plurality of segments further comprises identifying text that is part of a same medically-related intervention; wherein segmenting, by the computer system, at least a portion of the extracted content into the first plurality of segments further comprises identifying text that is part of a same medical-related intervention based at least in part on one or more of punctuation or indentions; wherein the analytics engine comprises a text extraction module, an entity alignment module, and a pattern matching engine and/or a machine learning engine; wherein the analytics engine comprises a text extraction module, an entity alignment module, a negation detection module, a syntactic analysis module, a pattern matching engine, and/or a machine learning engine; using a pattern matching engine and/or a machine learning engine to identify content that is to be included in the first plurality of segments; wherein identifying and extracting content from the clinical decision support document further comprises identifying content related to medicine dosages and identifying content related to a vital signs measurement; wherein the first segment, corresponding to the first item, does not include any words in common with the first item; generating an assessment document indicating how many interventions have and have not been verified in two or more categories of intervention.

An example aspect provides a method of analyzing a clinical decision support (CDS) document, the method comprising: receiving at a computer system, including hardware and comprising an analytics engine, a clinical decision support document; accessing, by the computer system, reference content corresponding at least in part to the clinical decision document; using the computer system, identifying and extracting medical intervention content from the clinical decision support document; segmenting, by the computer system, at least a portion of the extracted medical intervention content into a first plurality of segments including at least a first segment, comprising a first set of text, and a second segment comprising a second set of text; determining, by the computer system, if the first segment corresponds to at least a first item included in the reference content, the first item comprising a third set of text different than the first and second sets of text; at least partly in response to determining that the first segment, comprising the first set of text, corresponds to the first item included in the reference content, the first item comprising the third set of text, causing a report to include an indication that the first segment corresponds to the first item included in the reference content; determining if a second item included in the reference content corresponds to at least one of the first plurality of segments; at least partly in response to determining that the second item included in the reference content does not correspond to at least one of the first plurality of segments, causing the report to include an indication that the first plurality of segments fails to include at least one segment that corresponds to the second item included in the reference content. The foregoing example method may optionally include only a subset of the foregoing actions.

The foregoing example method may optionally further comprise one or more of the following: wherein identifying and extracting content from the clinical decision support document further comprises identifying content related to medicine dosages and identifying content related to a vital signs measurement; wherein determining if the first segment corresponds to the first item included in the reference content further comprises determining if the first segment comprises a functional synonym using different terminology with respect to the first item included in the reference content; determining whether a first character string in the clinical decision support document corresponds to a network protocol and at least partly in response to determining that the first character string in the clinical decision support document corresponds to a network protocol, excluding the first character string from the first plurality of segments; determining whether a first character string in the clinical decision support document exceeds a first number of words or characters and at least partly in response to determining that the first character string in the clinical decision support document exceeds the first number of words or characters, excluding the first character string from the first plurality of segments; at least a portion of the extracted content into the first plurality of segments further comprises identifying text that is part of a same medical-related intervention; wherein segmenting, by the computer system, at least a portion of the extracted content into the first plurality of segments further comprises identifying text that is part of a same medical-related intervention based at least in part on one or more of punctuation or indentions; wherein the analytics engine comprises a text extraction module, an entity alignment module, and a pattern matching engine and/or a machine learning engine; wherein the analytics engine comprises a text extraction module, an entity alignment module, a negation detection module, a syntactic analysis module, a pattern matching engine, and/or a machine learning engine; wherein identifying and extracting content from the clinical decision support document further comprises identifying content related to a medical intervention; wherein identifying and extracting content from the clinical decision support document further comprises identifying content related to medicine dosages; wherein identifying and extracting content from the clinical decision support document further comprises identifying content related to a vital signs measurement; wherein the first segment, corresponding to the first item, does not include any words in common with the first item; generating an assessment document indicating how many interventions have and have not been verified in two or more categories of intervention.

An example aspect provides an analytics system, comprising: at least one processing device comprising hardware; non-transitory media comprising a text extraction module, an entity alignment module, and at least one or a pattern matching engine or a machine learning engine, the when executed by the at least one processing device, are configured to cause the analytics system to perform operations comprising: receiving a clinical decision support document; accessing reference content corresponding at least in part to the clinical decision document; identifying and extracting medical intervention content from the clinical decision support document; segmenting at least a portion of the extracted medical intervention content into a first plurality of segments including at least a first segment, comprising a first set of text, and a second segment comprising a second set of text; determining if the first segment corresponds to at least a first item included in the reference content, the first item comprising a third set of text different than the first and second sets of text; at least partly in response to determining that the first segment, comprising the first set of text, corresponds to the first item included in the reference content, the first item comprising the third set of text, causing a report to include an indication that the first segment corresponds to the first item included in the reference content; determining if a second item included in the reference content corresponds to at least one of the first plurality of segments; at least partly in response to determining that the second item included in the reference content does not correspond to at least one of the first plurality of segments, causing the report to include an indication that the first plurality of segments fails to include at least one segment that corresponds to the second item included in the reference content.

The foregoing example system may optionally further comprise one or more of the following: wherein identifying and extracting content from the clinical decision support document further comprises identifying content related to medicine dosages and identifying content related to a vital signs measurement; wherein determining if the first segment corresponds to the first item included in the reference content further comprises determining if the first segment comprises a functional synonym using different terminology with respect to the first item included in the reference content.

BRIEF DESCRIPTION OF THE DRAWINGS

Embodiments will now be described with reference to the drawings summarized below. These drawings and the associated description are provided to illustrate example embodiments, and not to limit the scope of the invention.

FIGS. 5A, B, C illustrate example user interfaces.
FIG. 7A illustrates an example status report.
FIG. 7B illustrates an example intervention user interface.

DETAILED DESCRIPTION OF PREFERRED EMBODIMENTS

Figure 1:
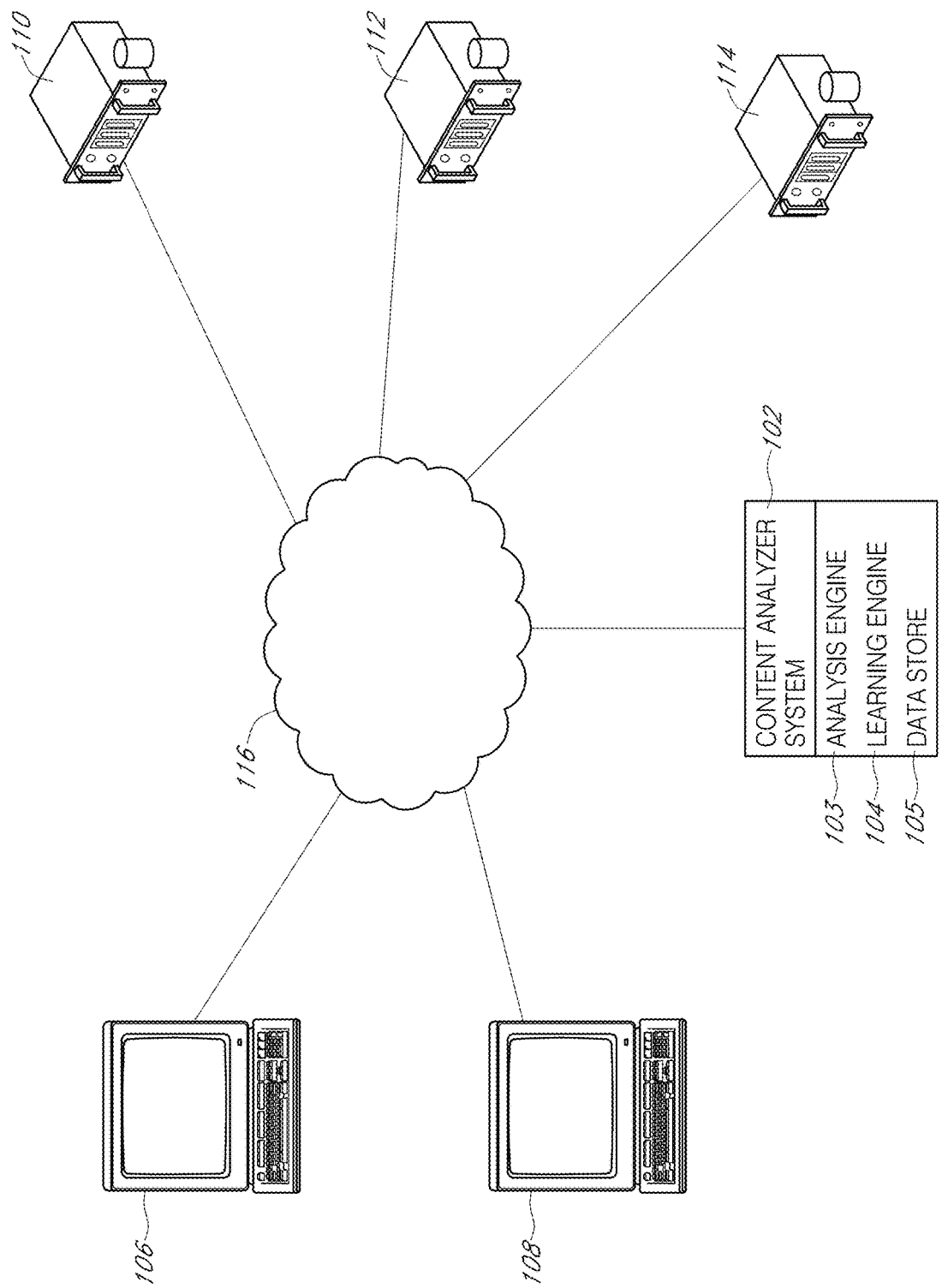
FIG. 1 illustrates an example architecture.

Systems and methods are described that provide automated content analysis.

Conventionally, providers need to assess their clinical decision support (CDS) content manually through expensive, lengthy, inconsistent, error prone, review cycles. Due to the lack of resources, time and knowledge, providers may be discouraged from keeping, or are simply unable to keep their content adequately current. Further, even when providers may attempt to maintain their CDS content, the lengthy and spaced apart review cycles typically used may result in CDS content that does not include the latest available updates. Further, due to the error prone nature of conventional approaches, even when such review cycles are timely performed, the result may fail to identify content that is not current, may erroneously identify current content as not current, or may replace content that is not current with the wrong content.

Certain embodiments described herein may be used to overcome some or all the deficiencies of conventional approaches noted above with respect to updating CDS content.

As similarly discussed above, certain example embodiments provide a system (sometimes referred to as a content analyzer for convenience) that analyzes and assesses content, such as clinical decision support (CDS) content, against reference content in a variety of forms. By way of example and not limitation, the reference content may comprise some or all of the following: clinical guidelines, clinical guidelines checklists, FDA checklists, FDA safety alerts, KBC data sources, regulations, new findings, other changes to clinical evidence, other types of reference content, etc. By way of example and not limitation, the CDS content may comprise some or all of the following: order sets, care plans (e.g., interdisciplinary plans of care (iPOC)), clinical decision support rules, multi-parameter alerting, etc. The CDS content and the reference content may be in a PDF format, word processing format, XML format, a text file format, or other format.

The system may comprise an analytics engine that automatically analyzes and assesses content. For example, using the analytics engine, the system may identify deficiencies and consistencies in a CDS document, relative to reference content, and the system may optionally generate a report indicating where a CDS document is deficient relative to reference content (where the deficiency indication may optionally include one or more items from the reference content that are missing from the CDS document) and/or where the CDS document is consistent relative to the reference content. The system optionally generates and reports update recommendations to be incorporated into the CDS document. Thus, the system may be used to better ensure that CDS content, such as that of a hospital (or entity controlling multiple hospitals) or other medical service provider, is current with new clinical guidelines and other reference content. Optionally, the system continuously or periodically harmonizes and standardizes CDS documents throughout a medical service provider's organization (e.g., across multiple departments or multiple hospitals), resulting in better medical treatment outcomes for patients.

Optionally, the reports and/or recommendations may be generated and accessed by the service provider(s) in substantially real time. Optionally the reports and/or recommendations may be generated in a machine readable format (e.g., in a digital format, a QR code, other bar code format, etc.) and input to and consumed by an EHR (Electronic Health Record) system (e.g., directly by an EHR system, without requiring another intermediate system to preprocess the reports/recommendations for consumption by the EHR).

As will be described in greater detail below, the content analyzer system may receive one or more documents, such as CDS documents, as input. The CDS documents may be developed and/or provided by an entity that develops CDS documents for different medical service providers (e.g., provides a library of CDS documents), or may be developed by the medical service providers themselves. The CDS documents may be developed and/or provided by the same entity that controls the content analyzer system. Thus, optionally, the content analyzer system may analyze CDS documents developed by the entity that controls the content analyzer system and/or CDS documents from the medical service providers.

The content analyzer system may identify and extract relevant content from such documents, compare some or all of the extracted content with one or more items of reference content, and generate and provide an assessment report, and optionally provide markups of the CDS documents. For example, the assessment report and/or the CDS document markup may indicate content in the CDS content that is current, that is not current, and for content that is not current, identify from the reference content the current content that should be included in the CDS documents, and/or provide recommendations as to updates to the CDS documents. Thus, for example, a new version of the CDS document may be generated by the system, the new version including some or all of the updated content from the reference content.

As noted above, the CDS content and the reference content may be in a variety of different formats. By way of example, the CDS content may be an electronic document in the form of a PDF file format, a word processing document format, an EHR (electronic health record) document format, a comma delimited format, a document produced using optical character recognition, a mixture of two or more of the foregoing formats, or other type of document format. The CDS content may contain text or graphics/photograph/video elements, or a mixture of text and graphics/photograph/video elements. The text may optionally comprise field identifiers and corresponding data. Optionally, the field identifiers may generally be static, while the field data may be variable. The CDS document content may be arranged in sections and subsections. Optionally, the content analyzer converts the CDS and/or reference content to a common format (e.g., a PDF format, a word processing format, a text file, or other format).

Optionally, some or all of the CDS documents may be accessed over a network from another system, such as a system associated with a medical institution, such as a hospital, clinic, doctor's office, therapist, etc. Optionally, in addition or instead, some or all of the CDS documents are stored local to the content analyzer system. Optionally, some or all of the reference content may be accessed over a network from another system, such as that of a research institution (e.g., a university, research hospital, laboratory, etc.), government entity, or standards institution. Optionally, in addition or instead, some or all of the reference content is stored local to the content analyzer system.

The analytics engine may comprise some or all of the following modules.

A text extraction module may be configured to identify and extract relevant content and/or non-relevant content from a CDS document. The text extraction module may optionally chunk such extracted relevant content into segments. For example, the extraction module may be configured to identify and extract relevant medical intervention content in the body of the CDS document, or in a header or footer of the CDS document. The medical intervention content may comprise checklist items, sentences, paragraphs and/or other content. The medical intervention content may be directed to processing a patient, treating a patient (e.g., providing medication, surgical procedures, therapy, diet, etc.), examining a patient, diagnosing a patient, and/or the like.

Pattern matching (e.g., using user defined rules) and/or machine learning (e.g., to build algorithms/models/fuzzy rules) may be used to identify the relevant content. For example, in order to determine which content is related to a medical intervention, pattern matching and/or machine learning may be used. Pattern matching algorithms may encode expert knowledge as logic rules. Machine learning algorithms may learn such logic rules from example data without having to have been programmed with the rules. By way of example, machine learning may be useful to specify fuzzy rules that are hard to describe manually.

By way of illustration, several optional example techniques for identifying relevant and non-relevant content will now be provided, although other techniques may be used in addition or instead.

If a character string begins with the characters "http" is identified, the text extraction module may determine that that the character string is a location locator (e.g., a URL) providing a link to other content, and so may designate the character string as non-relevant content (non-intervention content). Therefore, such character string may be stripped out/not included in the extracted content. Other initial character strings (e.g., signifying a type of protocol, such as HTTPS:, gopher:, wais:, ftp:) may similarly indicate that the following text is non-intervention content.

By way of further example, if the text extraction module identifies character strings (e.g., line items in the CDS document) related to medicine dosages (e.g., a quantity/volume of medication, such as milligrams or "cc"), the text extraction module may determine that the character string is likely directed to patient medication, and hence is relevant content with respect to a medical intervention.

By way of still further example, because medical intervention content is often in the form of a relatively short line item, if the text extraction module identifies a relatively long sentence (e.g., 8 or more words, although other lengths may be used, such as 6, 7, 9, 10, 11, 12, or 13 or more words) in the CDS document, the text extraction module may classify the sentence as likely non-relevant content (e.g., it may be determined to be "reminder" text as opposed to medical intervention text), even if the sentence includes references to medication or dosages. [0032] Optionally, a probability may be calculated as to the likelihood that a given portion of content is relevant/non-relevant. For example, to be conservative, if the system determines that there is a 10% or greater probability that a given portion of content is relevant, it may be included as relevant content, and if there is less than a 10% probability that the content is relevant, it may be excluded as non-relevant content. Other thresholds may be used (e.g., 1%, 5%, 25%, 30%, 40%, 50%, 60%, or other threshold) for determining what content is to be categorized as relevant or non-relevant. A human may optionally then review the content identified as relevant (or non-relevant) to determine if it is indeed relevant. Optionally, content within a certain range of probability (e.g., between 10%-90%, 5%-95%, 10%-75%, etc.) as being relevant is highlighted by the system to the reviewing user as being more uncertain with respect to its categorization than other content (e.g., content with a 90% or 95% probability of being relevant).

With respect to machine learning, a machine learning module may automatically determine which content features and/or thresholds are to be used to determine whether content is to be designated as relevant/non-relevant and construct or modify a model accordingly. Optionally, the features may be specified by a human, and the machine learning module may determine or modify thresholds. Examples of features may optionally comprise one or more of text length, presence of a medication term, medical intervention language, context (e.g., whether an immediately preceding portion of content is a CDS section, making it more likely that the current portion of content is not relevant), etc. The machine learning module may be trained by feeding the machine learning module training content that is known to be relevant content and by feeding the module content that is known not to be relevant. The machine learning module will then examine the content and classify it as relevant or non-relevant. The machine learning module is then informed whether its classification was correct or in error, and the module may then refine its model based at least in part on such feedback, thereby learning how to classify content as relevant or non-relevant.

For example, the machine learning module may determine/learn different weights for different features, apply the weights to features found in the content, and then classify the content accordingly (e.g., as relevant content or as non-relevant content).

As noted above, the text extraction module may optionally chunk such extracted relevant content into segments.

Such chunking process may identify text that is part of the same intervention/line item and group such text as a segment. For example, the chunking process may look for punctuation (e.g., periods), indentions, new lines, etc., to determine where a given portion (e.g., section) of CDS content begins and ends. The chunking process may exclude non-relevant content from the segments.

An entity alignment module is configured to fire one or more algorithms to assess if a segment generated by the text extraction module satisfies/corresponds to a specific item of the reference content, even if the terminology is not literally the same and even if the segment and specific item do not have any words in common. For example, the entity alignment module may optionally select an algorithm by feeding one or more segments to the entity alignment module that corresponds to known validation data (which may optionally be manually generated, and which is known to correspond to the specific item of reference content), determine if the entity alignment module correctly determined if the segment satisfies/corresponds to the specific item of the reference content (based on the known correspondence), and if the determination is incorrect, then that algorithm will not be used, and if the determination is correct, then that algorithm may be used.

By way of illustration, the entity alignment module may determine that a CDS document segment "benazepril" satisfies an item "ACE Inhibitor" of a reference "Heart Failure checklist" document, even though the segment and item do not contain any of the same words. Optionally, pattern matching and/or machine learning algorithms may be used in determining whether a segment derived from the CDS document satisfies a corresponding item of the reference content. As noted above, pattern matching algorithms may encode expert knowledge as logic rules. Machine learning algorithms may learn such rules from example data, as described elsewhere herein in greater detail. Machine learning may be useful in defining fuzzy rules that are too complex to be expressed hard to describe manually. For example, with respect to such content as measuring vital signs, there may be an enormous variation in the way a intervention can be defined (e.g., the intervention 12 lead ECG can be written as: 12 lead, twelve lead ECG, ECG-12, 12ld ECG, Electrocardiogram, ECG, EKG etc.; however 'Exercise ECG', while having textual similarities to the phrase "ECG-12," refers to a different intervention), and so it would be very difficult or time consuming for a user to manually identify the universe of possible variations and exceptions for a given intervention, and hence is would be very difficult or time consuming to specify if a given segment satisfies a corresponding item of reference content. Thus, the entity alignment module may optionally use a learning engine which identifies features in order to determine whether a given segment corresponds to an item of reference content. For example, the machine learning module may determine/learn different weights for different features and build a model/fuzzy rules using such weights for a given entity alignment.

By way of illustration, the learning engine may determine that certain characters, such as greater than ">" or less than "<" signs, or "mg" may typically correspond to vital sign measurement content. By way of further example, the learning engine may determine that if a certain segment is determined to be vital sign measurement content, then the immediately following segment is more likely to be vital sign measurement content. By yet further example, the learning engine may determine that certain patterns correspond to a vital sign measurement.

Certain embodiments provide the feature of negation detection. Even though a given intervention is mentioned in both a client content text segment and in the reference content, the engine may be configured to ensure that the instructions for ordering/not-ordering the intervention in the client content are compliant with the reference content. By way of illustration, the engine may be configured to examine text of the reference content and/or the CDS text segment to determine whether the text being analyzed indicates that a certain intervention should or should not be performed. For example, if an item on a reference checklist reads "aspirin", then the engine ensures that the client segment text mentions aspirin without a negation (e.g. "avoid", "do not order", "no", "discontinue", etc.) in order to indicate that the client segment is compliant. Thus, the engine would not incorrectly identify the client segment as being compliant with the reference checklist if the reference checklist indicated that a specified intervention should be performed, and the client segment indicated that the same specified intervention should not be performed, even though both included a reference to the same intervention. Similarly, if an item on the reference checklist includes the text "avoid aspirin", then the engine ensures that either the phrase "aspirin" is not present on the client content at all, or if the phrase "aspirin" is present, it is present in association with (e.g., adjacent to) a negation phrase (e.g., "no aspirin", "discontinue aspirin", etc.) in order to indicate that the client segment is compliant. If the engine determines that the client content's use of negation (or lack thereof) does not functionally match that of the reference content, the engine will flag the client content as non-complaint, and report the non-compliance accordingly.

Certain embodiments optionally utilize core-concept analysis to determine, at least in part, whether certain client content (e.g., a phrase that may correspond to an intervention, where the phrase may include one or more words or proper names) matches certain reference content. For example, even though a given intervention present in the reference content is also mentioned in a sentence or segment of the client content, such intervention mention might not qualify as a match if the mention of the intervention in the client content is not the core concept of the client content sentence or segment.

By way of example, assume the reference content lists both clopidogrel and aspirin as interventions for unstable angina. The use of the phrase "clopidogrel" in the following example client content segment "Consider the administration of clopidogrel to patients with unstable angina who have a contraindication to aspirin", qualifies as a match for clopidogrel in the reference content, as it is a core concept of the segment. However, the mention of aspirin does not qualify as a match for aspirin in the reference content, since aspirin is not a core concept of this segment. A concept may be determined to be a core concept if it is the subject or direct object of the sentence. The system may optionally determine if a given phrase (e.g., an intervention) is a core concept by calculating a syntactic parse tree that represents the syntactic structure of the sentence. By way of example, optionally constituency-based parse trees, dependency-based parse trees, and/or hybrid dependency-constituency trees may be generated and used.

Figure 9:
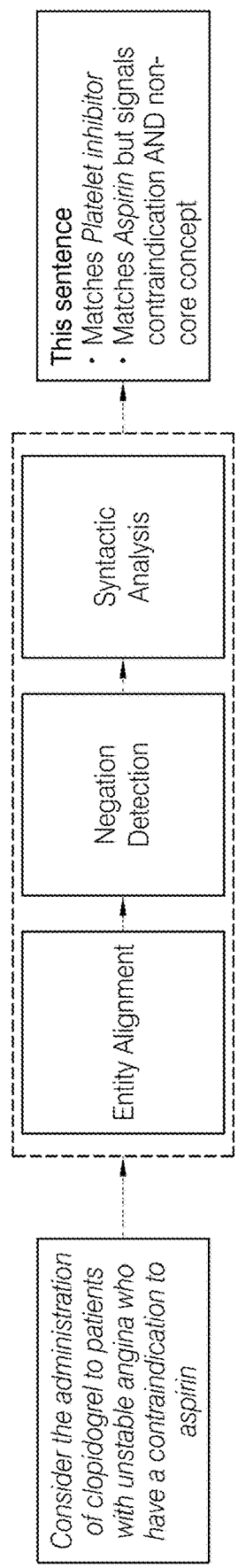
FIGS. 9-13 illustrate an example analytics engine and related processes.

FIG. 9 illustrates an example analytics engine that includes entity alignment, negation detection, and syntactic analysis modules providing the corresponding functionality discussed above. It is understood that one, two, or more modules may be used to perform the entity alignment, negation detection, and syntactic analysis functions. In the illustrated example, the client content segment "Consider the administration of clopidogrel to patients with unstable angina who have a contraindication to aspirin" is compared against reference content, that includes "platelet inhibitor" and "aspirin" as interventions for unstable angina, to determine if there are matches. The entity alignment module may process the segment as similarly discussed above.

For example, the analytics engine may determine that the segment reference to "clopidogrel" is a match for the phrase "platelet inhibitor" because clopidogrel is a type of platelet inhibitor even though the phrases "clopidogrel" and "platelet inhibitor" are not literally the same. The negation detection module may determine, from the phrase "contraindication", that the segment is signaling that "aspirin" is being listed as a contraindication, not as a recommended intervention (even though there is a literal, character-for-character match between the use of the phrase "aspirin" in the reference content and the use of the phrase "aspirin" in the client content segment). Thus, the negation module will indicate that the client content segment's use of the phrase "aspirin" is not a match. The syntactic analysis module utilizes a syntactic parse tree or other technique to determine that the client content segment does not refer to "aspirin" as a core concept, and so will also indicate that it is not a match.

Figure 10:
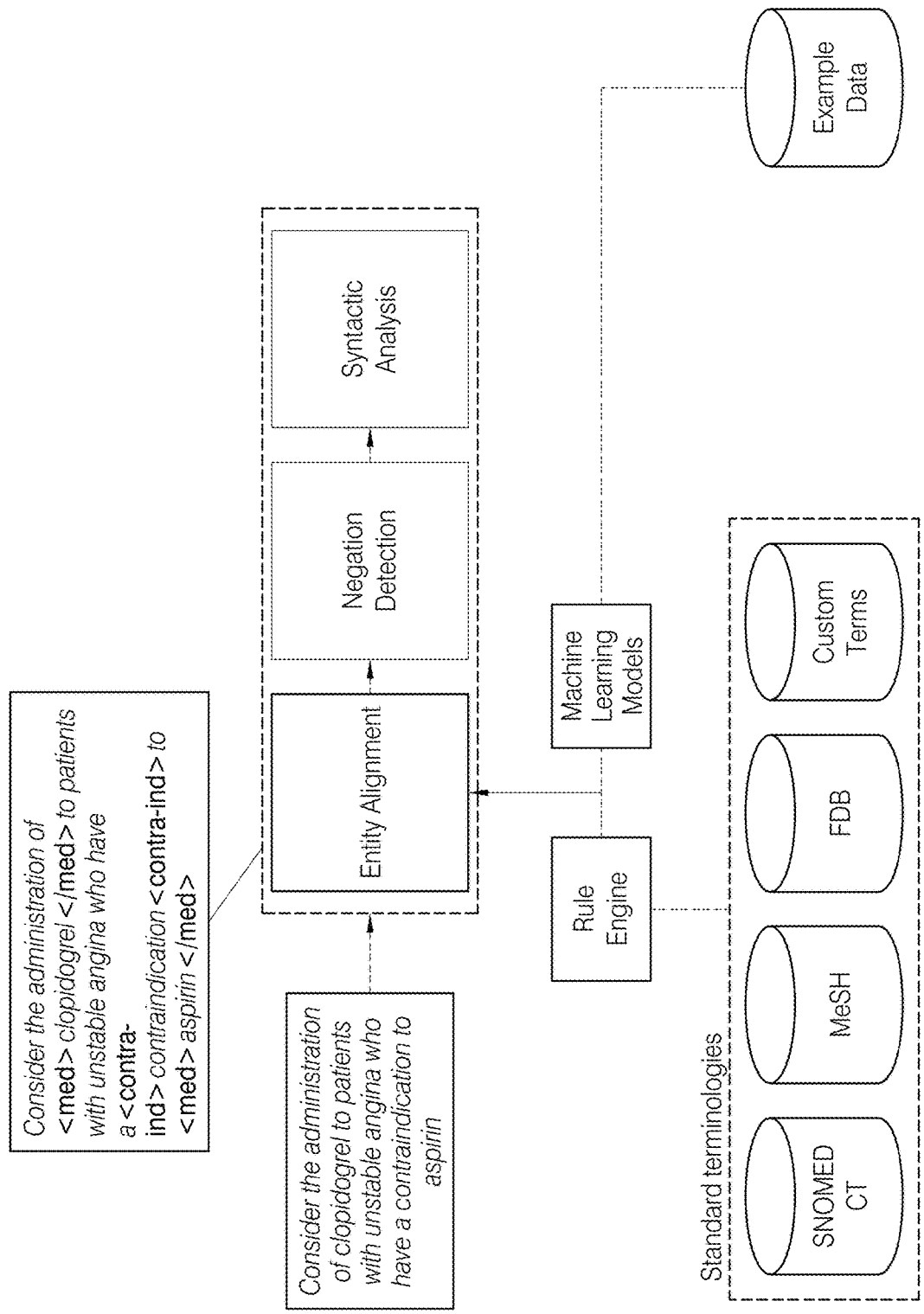

FIG. 10 illustrates an example of the operation of the entity alignment module in greater detail. As similarly discussed above, the entity alignment module may utilize a rule engine coupled to standard terminology sets and/or a machine learning module coupled to an example data source. The entity alignment module may analyze and parse the client content segment and identify and optionally tag phrases in the client content segment that corresponds to an intervention (e.g., a medicine) and phrases that indicate a contraindication. In this example, the entity alignment module identifies "clopidogrel" and "aspirin" as medications, and inserts corresponding categorization tags ("<med>" and "</med>") before and after "clopidogrel" and "aspirin". Similarly, the entity alignment module identifies the phrase "contraindication" as indicating a contraindication, and inserts corresponding categorization tags ("<contra-ind>" and "</contra-ind>") before and after "contraindication".

Figure 11:
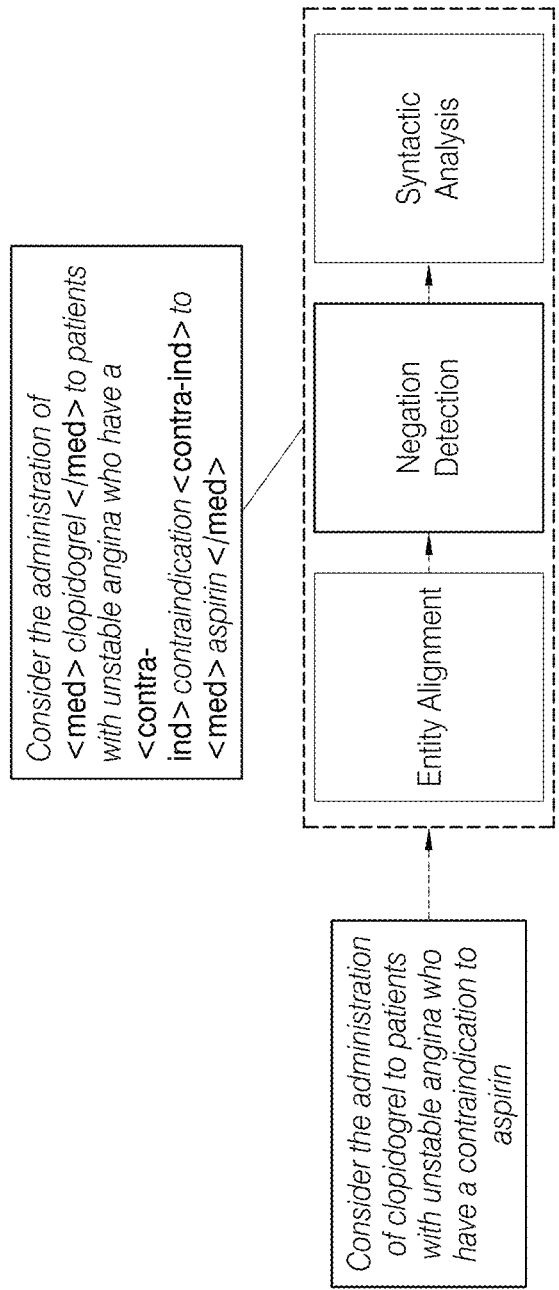

FIG. 11 illustrates an example of the operation of the negation detection module in greater detail. The negation detection module receives the tagged segment from the entity alignment module, and determines, using the tags, that the phrase "contraindication" is a negation of "aspirin", and so the use of "aspirin" in the segment is not a match for the intervention "aspirin" in the reference content.

Figure 12:
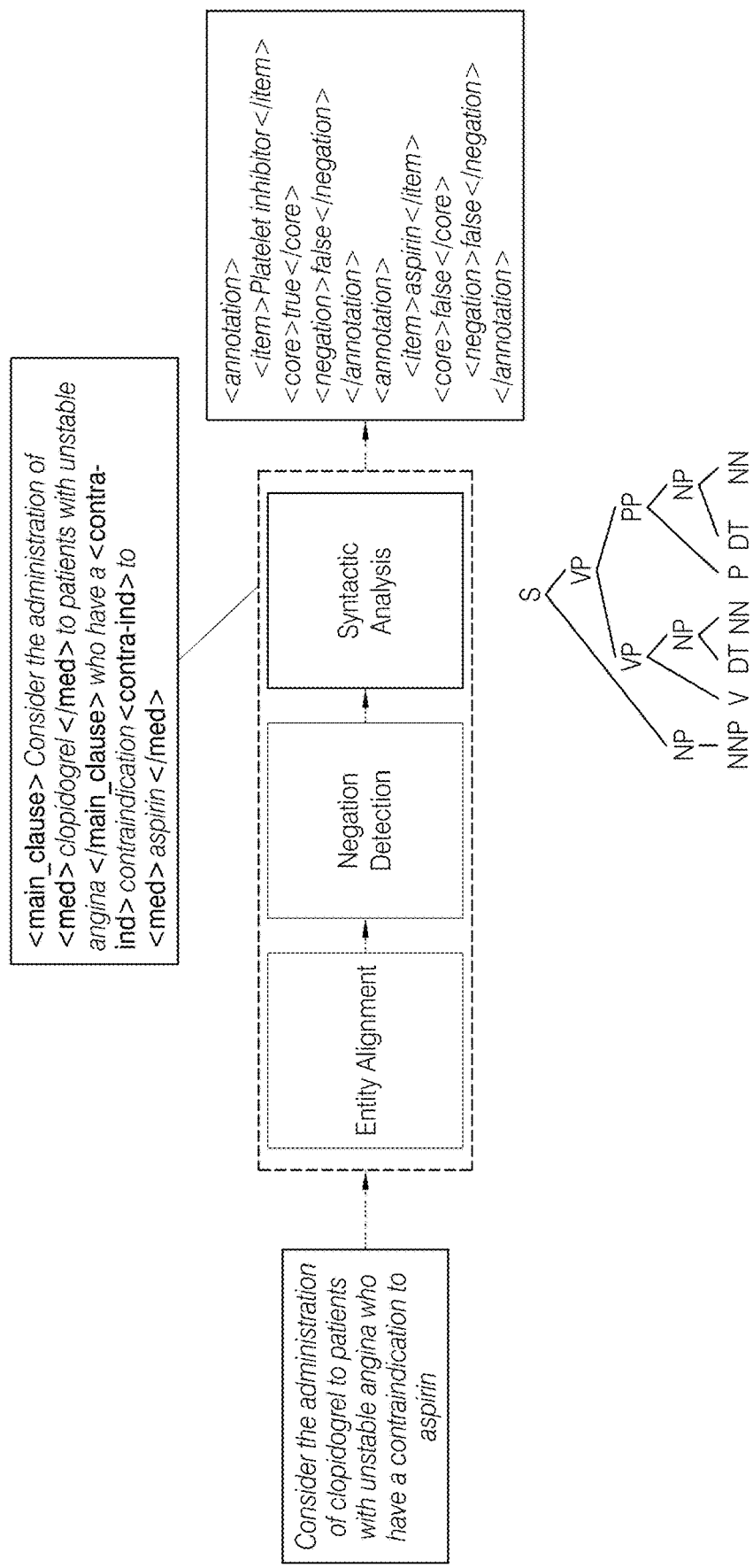
Figure 13:
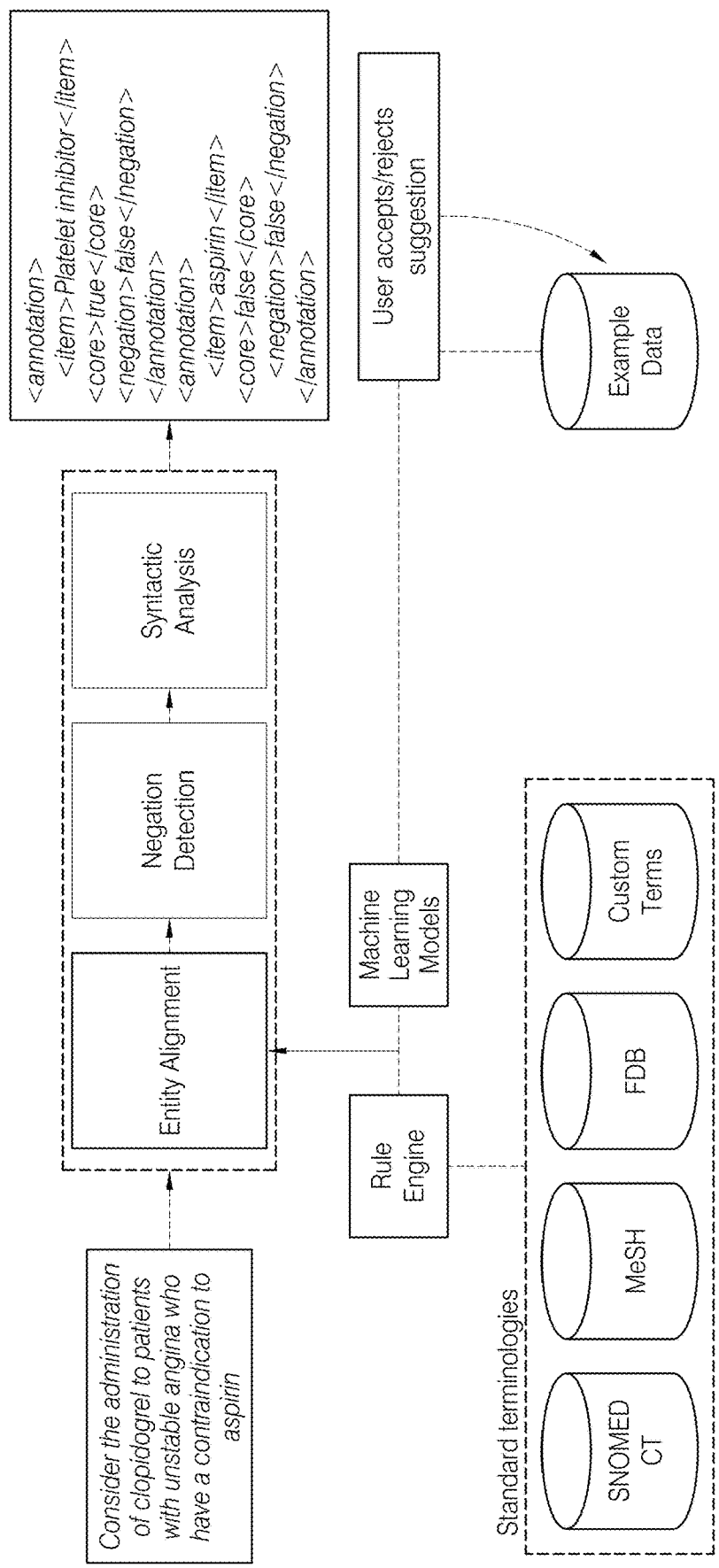

FIG. 12 illustrates an example of the operation of the syntactic analysis module in greater detail. The syntactic analysis module receives the tagged segment from the negation detection module. As illustrated, the syntactic analysis module generates a syntactic parse tree to identify the main clause in the segment. For example, a syntactic parse tree may include a sentence ("S") as the top-level structure. The tree also may sometimes also include one or more verb phrases ("VP"), which serve as predicates, noun phrases ("NP"), determiners ("DT"), prepositional phrases ("PP"), nouns ("NN"), proper nouns ("NNP"), adjectives, plural nouns, singular nouns, etc. In this example, based on the parse tree, the syntactic analysis module inserts corresponding "main_clause" tags before and after the identified main clause "Consider the administration of clopidogrel to patients with unstable angina", while the phrase "who have a contraindication to aspirin" is not included in the main clause. The analytic engine outputs its analysis, indicating that "clopidogrel" is a core concept that matches the phrase "platelet inhibitor" from the reference content, and that "aspirin" is negated/contraindicated and is not a core concept and is not a match for the phrase "aspirin" from the reference content.

Additionally, for certain medications, the engine takes into consideration medication dosage to determine whether the client content complies with the reference content or not. Thus, certain embodiments analyze the client content and the reference content to ensure the dosage in each content for a given medication matches (although they may use different units for measurements, in which case the engine may convert one or both of the dosages to a common unit). By way of example, a high dose of anticoagulant may be needed for anticoagulant effect but a low dose of anticoagulant may be needed for DVT prophylaxis. If the engine determines that the dosages do not match (optionally within a certain upper and/or lower threshold range), the engine will flag the client content dosage as non-complaint, and report the non-compliance accordingly.

As similarly discussed above, training data may be used to train the entity alignment module learning engine. For example, the entity alignment learning module may be trained by feeding the module training terms/segments that are known to be equivalent and optionally segments that are known to be not equivalent, where the learning machine is to determine on its own which features of those segments (e.g., specific terms, prefixes or suffixes, certain patterns, etc.) are good indicators to build rules upon for discriminating between different sets of segments. The entity alignment module learning module will then examine a separate set of test segments and classify them as equivalent or non-equivalent. The learning module is then informed whether its classification was correct or in error, and the module may then refine its model based at least in part on such feedback.

For example, a machine learning process may optionally collect positive and negative cases from corrections performed by users of the system and refine its rules as described above. For example, the positive and negative cases may be collected implicitly and/or explicitly. The implicit collection of cases may be performed by tracking and storing a record of user corrections to assessments generated by the system. The explicit collection of cases may be performed by having medical experts manually compare and match terms in a set of CDS documents to one or more items of reference content (e.g., a checklist).

With respect to pattern matching, the pattern matching process may access one or more data sets. For example, the data sets may be health content terminology data sets, such as SNOMED CT, ICD-9, ICD-10, CPT, MeSH, FDN, RxNorm, LOINC, etc. The pattern matching process may extract keywords from a document, such as a scoring notes document prepared by medical experts (e.g., manually and/or via an automatic system). A given item of reference content (e.g., a checklist) may be linked to one or more scoring notes. The scoring notes may contain inclusion or exclusion criteria, such as synonyms for how a checklist items may appear in the CDS documents. Thus, for example, the scoring notes may optionally indicate equivalent terms for a given keyword. The scoring notes may also optionally indicate non-equivalent terms for a given keyword, where the non-equivalent terms may appear similar to (e.g., have slightly different spelling than) the given keyword but are functionally different.

The keywords may optionally be expanded by crawling terminology data sets, such as the health content terminology data sets discussed above, which may be stored remotely or locally. For example, a given data source may be structured (e.g., a structured database or look-up table) which may identify synonyms for a given term/keyword. Thus, the pattern matching process may use a given keyword as an anchor, access the structured data source, locate the given keyword in the structured data source, access terms identified by the structured data source as a synonym for the given keyword, and then use such synonyms to determine if a given segment in the CDS document satisfies (is an equivalent of) a term in the reference content.

The process may build a search query that takes a segment as input, determines if it matches (in whole or in part) text in the reference document (e.g., matches exactly or matches as a "functional synonym" for the reference document text, as indicated by the keywords) and returns an indication as to whether there is a match or not. Optionally, if the CDS document comprises a checklist, the foregoing process may be performed for some or all items in the CDS document checklist. Optionally, even if a first match is found, the process may continue to compare the segment against additional portions of the reference document to determine if there is more than one match. Thus, a given segment may match more than one portion of text in the reference document, and a given potion of text in the reference document may match more than one segment from the CDS document.

A report generation module is configured to generate, based at least in part on the alignment assessment results, a report. The generated report may include an assessment document and/or a markup of the CDS document (e.g., the original CDS document received from or used by the service provider). For example, the markup of the CDS document may indicate where the CDS document is deficient relative to the reference content and/or where the CDS document is consistent relative to the reference content.

For example, the report generator module may reproduce the CDS document, code (e.g., via color coding, underlining, bolding, icons, checkmarks, positioning, font, or other visually distinguishing indicia) the original text that is consistent with the reference source (e.g., is the same or is a functional synonym of text from the reference source), and insert differently coded text (e.g., via color coding, underlining, bolding, italics, positioning, font, and/or other visually distinguishing indicia that is different than that for the original text that is consistent with the reference source text) that is missing from the original CDS document but that is present in the reference document.

For example, the original CDS document text that is consistent with the reference source may be color coded green, and the inserted text that is missing from the original CDS document but that is present in the reference document may be color coded red. This coding makes it easy for a user to quickly understand what is missing from the original CDS document, and how to improve the CDS document. The assessment report may optionally be in the form of a checklist corresponding to the items in the reference document, where a checkmark (or other indicia) is provided to indicate whether an item in the reference document is present in the CDS document (even if the CDS document utilizes different, but functionally equivalent terminology).

The content analyzer system may be used to assess CDS content against CDS checklists, monitor CDS content and alert service providers in case of FDA drug withdrawals (or other significant alerts), combine different CDS documents into a single unifying document, etc. It is understood that an order set, as used herein, generally includes a grouping of orders, and enables standardization of the ordering process for a common clinical scenario, such as might occur in a hospital setting. Examples of order sets include admission order sets for use in admitting a patient to a given service or venue, diagnosis order sets for use in standardizing care orders for respective common clinical diagnoses, and convenience order sets for use in standardizing orders for respective clinical goals (e.g., a treatment procedure).

Another optional feature of system is the repeated retraining of the classification mechanism based on new incoming data (e.g., user feedback received in a feedback loop) to improve system accuracy in identifying (e.g., using pattern matching and/or machine learning) CDS document deficiencies and consistencies with respect to reference content. For example, users can review classifications provided by the system and indicate whether a given classification is correct/incorrect. By way of illustration, if a user indicates that a given term does not correspond to another term, the learning module may update its model to include a negative rule indicating that the two terms are not equivalent. Optionally, the feedback may be provided by members of a particular medical service provider (e.g., a hospital or association of hospitals), and such feedback may be used to modify a given pattern matching rule. Optionally, such feedback from a given medical service provider will be used to only modify the pattern matching rules for the medical service provider, but not the pattern matching rules of other medical service providers (although optionally such feedback may be used for other medical service providers). Optionally, such feedback from a given medical service provider will be used to modify the corresponding machine learning model/rules generally (including those of other medical service providers), although optionally such feedback may be used to only modify the learning model/rules of the medical service provider providing the feedback.

Referring to FIG. 1, an example environment is illustrated. An example content analyzer system 102 may include an analysis engine 103, an optional learning engine 104, and a data store 105. The data store 105 may store CDS documents, reference content, and/or other data and content discussed herein. The content analyzer system 102 may be coupled to a network 116 via a network interface device, which may include a local area network and/or a wide area network. For example, the network 116 may comprise the Internet. The content analyzer system 102 may communicate over the network 116 with one or more reference content provider systems 110, 112, 114 to access reference content, as discussed elsewhere herein. For example, the reference provider systems may include one or more research institutions, the FDA, the National Institute of Health, etc. The content analyzer system 102 may further communicate with one or more health care provider systems 106, 108, which may correspond to hospital computer systems, clinic computer systems, etc., to access CDS documents from such health care provider systems and/or to provide reports and recommendations to such health care provider systems. The various illustrated components may generally interact, process data, and provide or receive reports as similarly discussed elsewhere herein.

Figure 2:
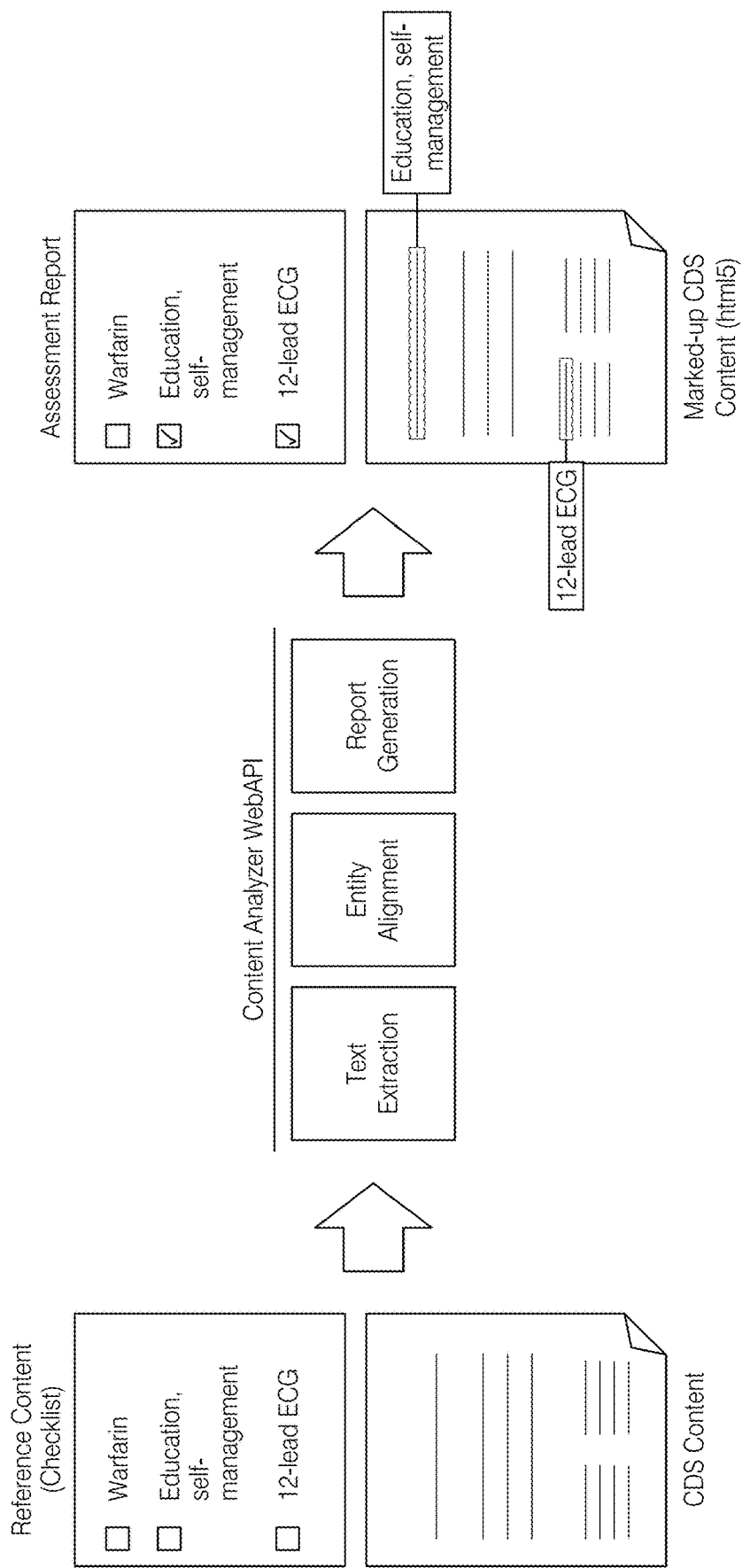
FIG. 2 illustrates an example content analyzer information flow.

FIG. 2 illustrates an example content analysis process. The content analyzer system receives the reference content from a reference content provider system. The content analyzer system may store the reference content in a local data store. In this example, the reference content is a checklist for a treatment procedure for a first medical condition, although other reference content may be used. The content analyzer system may also receive CDS content (e.g., in the form of a document) from a health care provider (or other source). The content analyzer system may optionally store the CDS content in a local data store. The CDS content may optionally include a checklist document for a treatment procedure for the same first medical condition. The content analyzer system may perform text extraction on the CDS content and/or the reference content. The text extraction process may identify and extract relevant content from the CDS content and optionally chunk the extracted relevant content into segments. An entity alignment process determines if a given segment satisfies a specific item of the reference content. By way of example, pattern matching and/or machine learning may be utilized in determining whether a given segment derived from the CDS document satisfies a corresponding item of the reference document.

A report generation process may be used to generate a report. The generated report may include an assessment document and/or a markup of the CDS document (e.g., the original CDS document received from the service provider). For example, the markup of the CDS document may indicate where the CDS document is deficient relative to the reference content (where the markup may include one or more items of reference content missing from the CDS document) and/or where the CDS document is consistent relative to the reference content (even if the language is not literally the same as in the reference content but is functionally equivalent). The marked-up CDS document may be in the form of a text file, a word processing document, an HTML document, or other form.

Optionally, in addition or instead, the assessment document and/or a markup of the CDS document may be provided in structured machine readable form and may be provided to, and ingested by another system or other software (e.g., which may be associated with a third party or the medical service provider). For example, a Web API (application program interface) may be provided to exchange data between systems. By way of illustration, the content analyzer web API may be utilized to receive the data from the reference content provider and/or the CDS content provider. The content analyzer web API be used to export the assessment report and/or marked-up CDS content to another system (e.g., the health care provider system).

Figure 3:
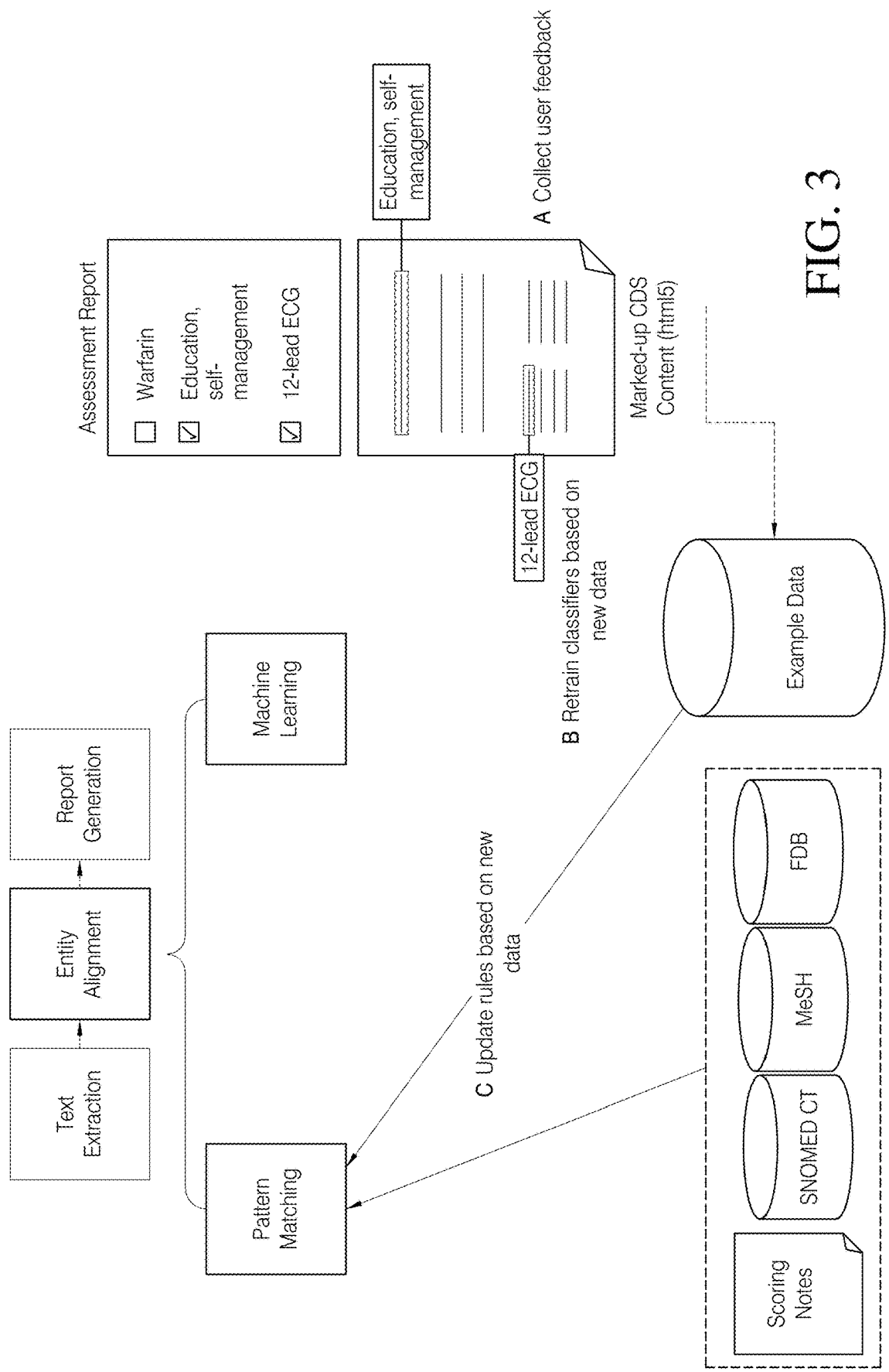
FIG. 3 illustrates an example analysis engine.

FIG. 3 illustrates an example analytics engine and a related analytics process as applied to a checklist, such as a clinical guideline checklist. Of course, the process may be applied to other types of content and documents. In this example, for a given item in the checklist, keywords are extracted from a scoring notes document (such as that described above). The keywords may be expanded by the analytics engine as similarly discussed above. For example, the analytics engine may crawl one or more data stores storing standard terminology terms, such as SNOMED CT, MeSH, or FDB terminologies. The analytics engine may build a search query based at least in part on the extracted keywords and/or the expanded keywords. The search query may take a text segment extracted from the CDS document as an input, determine if there is a match using pattern matching and/or machine learning, and return an indication, such as a true or false indication (or a percentage likelihood or other score indicating that there is or is not a match), to indicate whether or not the text segment matches the search query.

Optionally, a machine learning process is performed using a machine learning engine. For a given item in a reference checklist, the machine learning engine collects positive and negative cases from annotated CDS documents for training. The machine learning engine then trains a statistical model, taking as input a text segment extracted from a CDS document and returning a likelihood that the segment match a reference checklist item. The trained machine learning process may then be used to determine if checklist text segment matches the search query.

Figure 4:
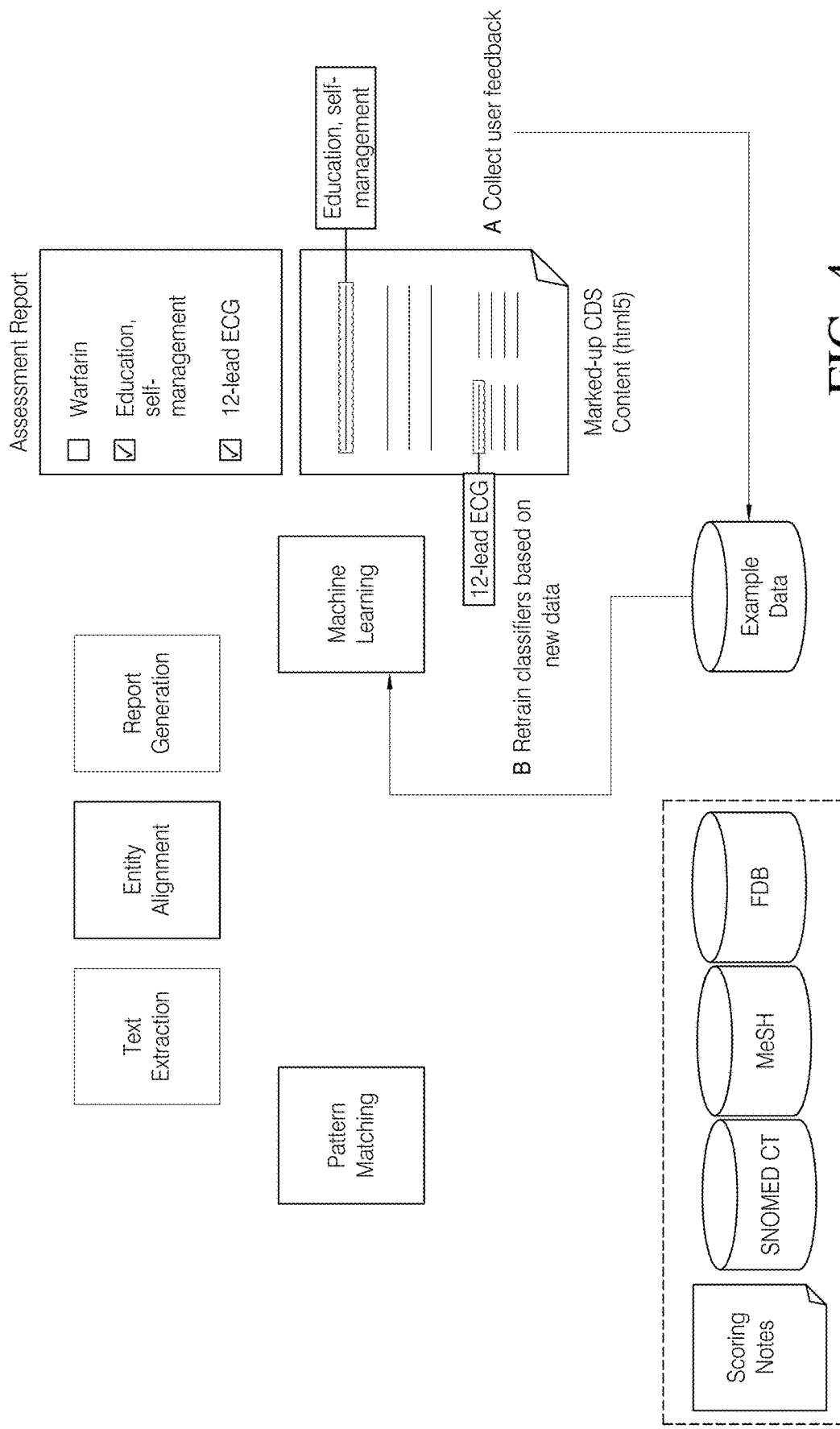
FIG. 4 illustrates an example learning engine.

Referring to FIG. 4, optionally, in order to improve the accuracy of the classification process, the classification process may be repeatedly retrained based at least in part on additional data, such as new incoming data. By way of example, the incoming data may be user feedback indicating whether a given system classification was correct or incorrect, as similarly described above. The user feedback may be entered via a user terminal and received by the system. The incoming data may be used to retrain the machine learning engine classifiers.

FIG. 5A illustrates an example user feedback interface. In this example, the segment "CHF pack/teaching" from a CDS document was not recognized by the system as being a match for a reference item "Education self-management", even though they are equivalent, and hence a match. The user can select the segment (e.g., by clicking on the segment), and a user interface, an example of which is illustrated in FIG. 5B, is displayed via which the user can specify the correct intervention, which in this example, is that "Education self-management" is a match for "CHF packet/teaching", and then instruct the system to save the association. The system may then record the equivalence for future analysis. Then, if the CDS document is submitted again to the system for analysis, the system determine, based on the recorded equivalence, that "CHF packet/teaching" does correspond to an item in the reference source ("Education self-management" in this example), and will cause the segment "CHF packet/teaching" to be highlighted (or otherwise coded) to indicate that it matches an item from the reference source, as illustrated in FIG. 5C.

In another example, the system may have incorrectly identified a segment as matching a reference item. The user can select the segment, and a user interface is displayed via which the user can specify the correct intervention, which in this example, is that they do not match, and optionally, that the segment corresponds to a different reference item. The system can record the lack of equivalence for future analysis.

Certain embodiments score the compatibility of the CDS content with the reference content, and track how much of and which CDS content has been verified to be consistent with the reference content. Such information may generated and calculated from data generated by the content analyzer system modules and then provided for display to a user (e.g., in the form of an assessment report dashboard). For example, the dashboard may indicate textually and/or graphically how many items (and/or what percentage of items) in a reference document have been verified to be present (and/or not verified to be present) in the CDS document being analyzed. A given item in reference document may optionally be associated with metadata indicating the type of information the item relates to (e.g., performance attributes (e.g., cost reductions, hospitalizations, etc.), and the dashboard may indicate how many (and/or what percentage) of items of a given type in the reference document have been verified to be present in (and/or absent from) the CDS document being analyzed.

Figure 6:
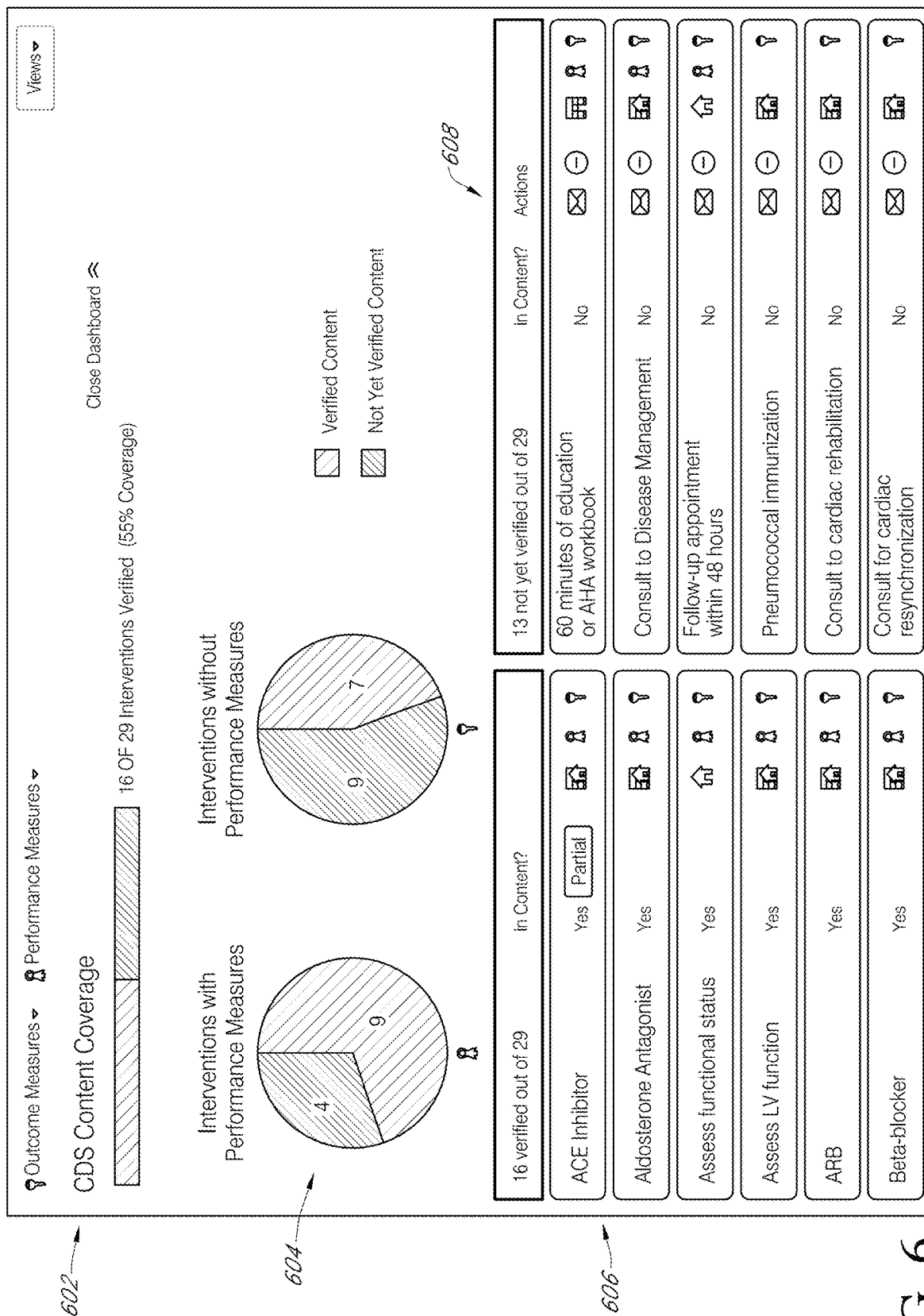
FIG. 6 illustrates an example assessment report.

FIG. 6 illustrates an example assessment report dashboard generated by the system for a given CDS document being analyzed. As noted above, text, graphs, and/or calculated numbers may be used to summarize the analysis finding. In order to generate the assessment report, the system may calculate how many interventions have and have not been verified and the percentage of interventions that have or have not been verified. In this illustrated example, a CDS Content Coverage bar chart graphical 602 illustrates how many reference source interventions have and have not been verified as being present in the CDS document. In addition, the report indicates the number of interventions that have been verified out of the total number of interventions. The report may also indicate content coverage broken down by two or more categories of intervention. In the illustrated example, coverage is broken down for two categories of interventions 602 (interventions with performance measures and interventions without performance measures). In the illustrated example, respective pie charts and cumulative numbers of verified and not verified content items are provided for each of the identified types of interventions. The illustrated report includes a list of interventions 606 from the reference source(s) that were found in the CDS document, with an indication as whether the intervention was fully or only partially found in the CDS document by the system. A partial match indication may indicate that an intervention has been found, however with indicators for relatively minor gaps. By way of illustration, a CDS document may list the term "Beta-blockers" with an adjacent blank line for the physician to fill in a beta-blocker medication. In this case, the system would return a match for the intervention "Beta-blocker" with a partial flag indicating that although the correct drug class ("Bet-blockers") was listed, a corresponding specific beta-blocker medication was missing. The illustrated report also includes a list of interventions 608 from the reference source(s) that were not verified as being found in the CDS document. Controls are provided via which the user can initiate actions regarding such non-verified actions (e.g., email action item to an appropriate entity to manage the non-verified content, or delete the intervention from the list).

As will now be discussed, the content analyzer system may track and report workflow status information. By way of illustration, the content analyzer system may identify certain tasks that are to be performed by a human. For example, the content analyzer system may determine that a CDS document is or may be missing one or more items as similarly discussed above. The content analyzer may then generate a list of tasks (e.g., non-verified items), and notify a user, such as a content manager, regarding the tasks. The user (or another user) may be assigned to complete the task (e.g., revise the CDS document to include the item or verify that the item is in the CDS document). The content analyzer system may track the workflow status of the task. For example, until the task is assigned to a person or organization to complete, the task may be designated as "waiting assignment," "not started" or the like. Once the task is assigned to a user, the task may be designated as "assigned." Once the assigned user has indicated, or the system otherwise determines that the task is complete, the task is designated as "complete."

FIG. 7A illustrates an example status report that may be generated by the content analyzer system. In this example, there is a list of interventions that were not verified by the system. A field is provided which indicates whether the intervention has been identified in the CDS document being analyzed (the "In Examiner Content" column). A "Section" column is provided which indicates in what section that intervention should be placed in the CDS content (e.g., "Patient Education," "Reminder," "Medication," Consult," etc.). A status column indicates the current status of the task (e.g., "not started," "assigned", "sent to assignee," "in progress," "complete"). An "Assignee" column indicates to what entity and/or individual the task has been assigned to. An action column includes various actions the user can initiate with respect to the corresponding task (e.g., email the task, delete task). In addition, an intervention details column may be provided indicating what category the intervention belongs to (e.g., performance measure, outcome measure). Optionally, the content analyzer system track and reports changes made by users and/or by the content analyzer system to CDS content.

FIG. 7B illustrates an example interface displaying details regarding an intervention (in this example, "Pneumococcal immunization") and optionally via which a user can provide a recommendation on how to address an intervention that had been identified as missing. The user interface may "pop-up" over the user interface illustrated in FIG. 7A. The user interface made indicate the intervention section ("medication" in this example), status ("sent to Zynx" in this example), assignee (e.g., person's email address, which may include the assignee's name). The details may identify a subpopulation to whom the intervention applies (e.g., patients of a certain age that are at risk with respect to particular condition), outcome measures (e.g., cost, admission, current length of stay, mortality, readmission, subsequent length of stay, performance measures (e.g., as specified by a government agency or an insurance entity, such as a set of criteria defined by the Centers for Medicare and Medicaid Services (CMS) to evaluate how well hospitals care for patients with certain conditions, or the Joint Commission for National Hospital Inpatient Quality Measures (e.g., "CMS ARRA 2," "CMS NHQM," "TJC NHQM," etc.)), and/or evidence (optionally including a control via which a user can add an evidence link). The user interface may also present a list of actions other organizations (e.g., of similar type to the organization to which the CDS document being analyzed belongs) take with respect to the intervention (e.g., "order set: Heat failure admissions; section title: medications other; line item: Immunizations").

Figure 8:
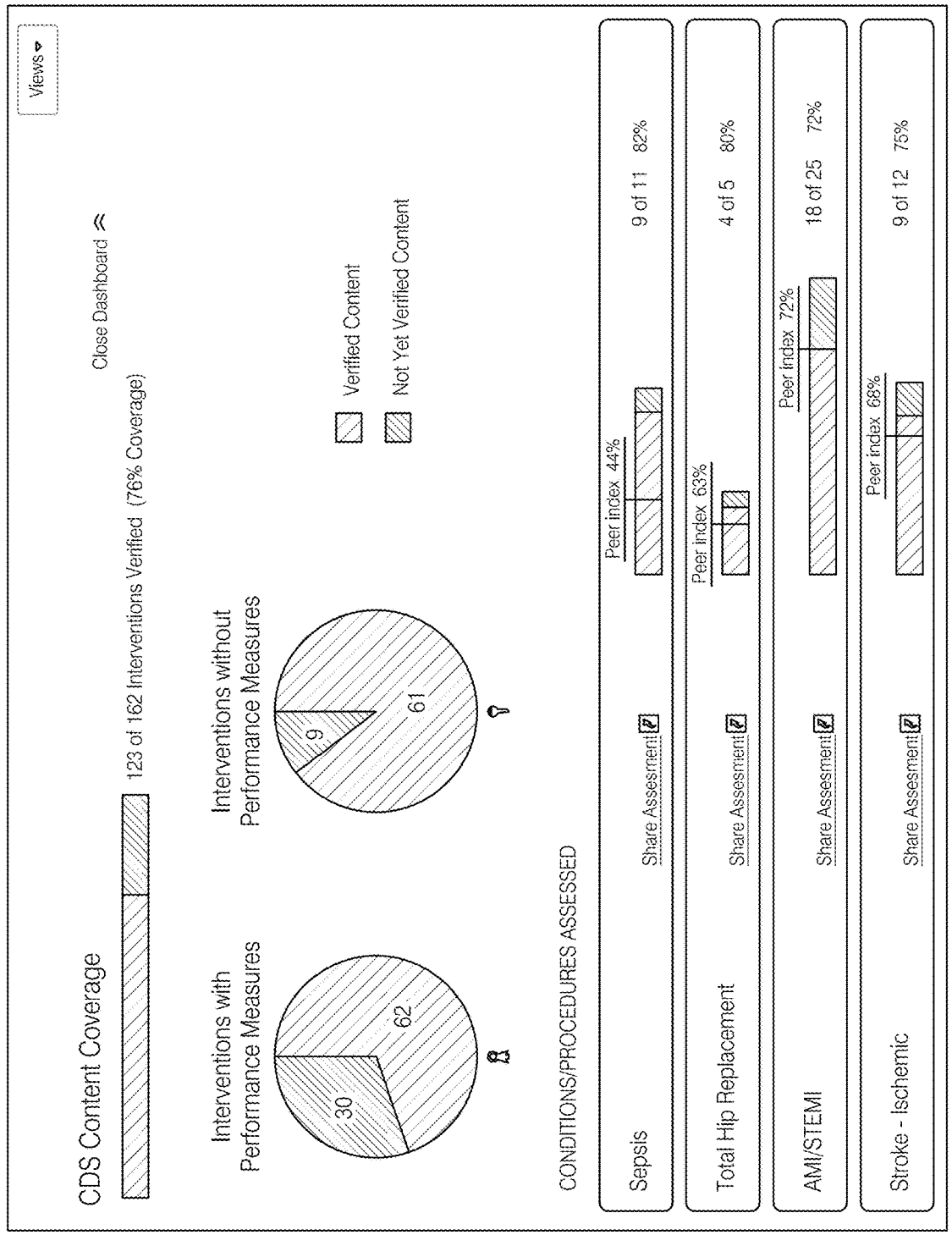
FIG. 8 illustrates an example performance report.

Certain embodiments generate comparative data for different service providers or groups of service providers. FIG. 8 illustrates an example of a report illustrating the relative performance of different service providers with respect to how complete their CDS documents are (e.g., as determined by comparing such CDS documents to reference content). The content analyzer system may track and aggregate such data for each service provider, which may be obtained via the processes described above, and report to a given service provider how well the service provider is doing as compared to other similar service providers. For example, the system may identify and compare the performance of a hospital of a given type (e.g., a university hospital, a city-run hospital, a community hospital) relative to hospitals of the same type. This enables service providers to determine how well they are performing compared to other, similar service providers, against a state or national average, etc., and to identify best practices. The comparisons may compare the number and/or percentage of verified and unverified interventions (with and without performance measures), optionally broken down by category.

Thus, as descried herein, certain example embodiments provide systems and automated processes that analyze and assess content, such as clinical decision support (CDS) content, against reference content and identify potential deficiencies. This may enable service providers, such as medical service providers, to conform their content and procedures to recent related developments, such as FDA safety alerts, new findings, new regulations, and the like.

This may further enable medical service providers to provide patients with medical care in accordance with current best practices.

The methods and processes described herein may have fewer or additional steps or states and the steps or states may be performed in a different order. Not all steps or states need to be reached. The methods and processes described herein may be embodied in, and fully or partially automated via, software code modules executed by one or more general purpose computers. The code modules may be stored in any type of computer-readable medium or other computer storage device. Some or all of the methods may alternatively be embodied in whole or in part in specialized computer hardware. The results of the disclosed methods may be stored in any type of computer data repository, such as relational databases and flat file systems that use volatile and/or non-volatile memory (e.g., magnetic disk storage, optical storage, EEPROM and/or solid state RAM).

While the phrase "click" may be used with respect to a user selecting a control, menu selection, or the like, other user inputs may be used, such as voice commands, text entry, gestures, etc. User inputs may, by way of example, be provided via an interface, such as via text fields, wherein a user enters text, and/or via a menu selection (e.g., a drop down menu, a list or other arrangement via which the user can check via a check box or otherwise make a selection or selections, a group of individually selectable icons, etc.). When the user provides an input or activates a control, a corresponding computing system may perform the corresponding operation. Some or all of the data, inputs and instructions provided by a user may optionally be stored in a system data store (e.g., a database), from which the system may access and retrieve such data, inputs, and instructions. The notifications and user interfaces described herein may be provided via a Web page, a dedicated or non-dedicated phone application, computer application, a short messaging service message (e.g., SMS, MMS, etc.), instant messaging, email, push notification, audibly, and/or otherwise. Optionally, user interfaces may be provided with editing tools, enabling users to select, cut, copy, paste, undo, redo, and otherwise edit user provided content and/or other content.

Data and reports described herein as being provided in human readable form may in addition or instead be provided in machine readable form in a manner suitable to be ingested by other systems and software (e.g., via a Web API). Conversely, data and reports described herein as being provided in machine readable form may in addition or instead be provided in human readable form.

The user terminals described herein may be in the form of a mobile communication device (e.g., a cell phone), laptop, tablet computer, interactive television, game console, media streaming device, head-wearable display, networked watch, etc.

The services and/or software may optionally be provided via a software as a service (SaaS) implementation or optionally via an application installed on user systems.

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the invention can be practiced in many ways. As is also stated above, the use of particular terminology when describing certain features or aspects of certain embodiments should not be taken to imply that the terminology is being re-defined herein to be restricted to including any specific characteristics of the features or aspects of the invention with which that terminology is associated.

What is claimed is:

1. A computerized, machine learning system, comprising:
   at least one processing device comprising hardware;
   non-transitory media comprising program code that when executed by the at least one processing device, are configured to cause the machine learning system to perform operations comprising:
     instantiating a machine learning module configured to process fuzzy rules to identify whether a segment from a clinical decision support (CDS) document satisfies a corresponding segment from a reference content comprising clinical guidelines;
     improving machine learning system accuracy in identifying CDS document deficiencies and consistencies with respect to reference content, by repeatedly training the machine learning module based on new incoming data,
     wherein improving machine learning system accuracy by training the machine learning module comprises repeatedly:
       collecting positive and negative cases from CDS documents,
       training the machine learning module using the collected positive and negative cases from CDS documents;
     receiving a clinical decision support document;
     accessing reference content corresponding at least in part to the clinical decision support document;
     identifying and extracting medical intervention content from the clinical decision support document;
     segmenting at least a portion of the extracted medical intervention content into a first plurality of segments including at least a first segment, comprising a first set of text, and a second segment comprising a second set of text;
     determining, using the machine learning module, if the first segment corresponds to at least a first item included in the reference content, the first item comprising a third set of text different than the first and second sets of text;
     determining, using the machine learning module, if a second item included in the reference content corresponds to at least one of the first plurality of segments;
     at least partly in response to:
       determining that the first segment, comprising the first set of text, corresponds to the first item included in the reference content, the first item comprising the third set of text, and
       determining that the second item included in the reference content does not correspond to at least one of the first plurality of segments;
     dynamically generating a version of the clinical decision support document that includes:
       a visual indication that the first segment corresponds to the first item included in the reference content; and
       a visual indication that the first plurality of segments fails to include at least one segment that corresponds to the second item included in the reference content.

2. The system as defined in claim 1, wherein determining if the first segment corresponds to the first item included in the reference content further comprises:

identifying and tagging phrases that correspond to a medical intervention;

identifying and tagging phrases that correspond to a contraindication;

based on one or more phrase tags, generating a syntactic parse tree comprising verb phrases, noun phrases, determiners, prepositional phrases, nouns, and/or adjectives;

using the syntactic parse tree to identify a main clause.

3. The system as defined in claim 1, wherein the machine learning module is configured to automatically determine which content features are to be used to determine whether content is to be designated as relevant and matching to the reference content and which content is to be designated as non-relevant and to construct or modify a model accordingly, wherein the features comprise one or more of text length, presence of a medication term, medical intervention language, use of a negation, or context, the operations further comprising:

using the model to identify and extract medical intervention content from the clinical decision support document;

using feedback with respect to the identification of the medical intervention content to refine the model.

4. The system as defined in claim 1, wherein identifying and extracting content from the clinical decision support document further comprises:

identifying content related to medicine dosages;
identifying content related to medicine units; and
identifying content related to a vital signs measurement.

5. The system as defined in claim 1, wherein determining if the first segment corresponds to the first item included in the reference content further comprises determining if the first segment comprises a functional synonym using different terminology with respect to the first item included in the reference content.

6. The system as defined in claim 1, wherein determining if the first segment corresponds to the first item included in the reference content further comprises determining if a phrase in the first segment comprises a core concept of the first segment.

7. The system as defined in claim 1, the system further comprising a negation detection and syntactic analysis system.

8. The system as defined in claim 1, wherein generating a version of the clinical decision support document that includes a visual indication that the first segment corresponds to the first item included in the reference content, further comprises using color coding, underlining, bolding, italics, positioning, or font in providing the visual indication that the first segment corresponds to the first item included in the reference content.

9. A method of analyzing a clinical decision support (CDS) document, the method comprising:

improving a computerized machine learning system accuracy in identifying CDS document deficiencies and consistencies with respect to reference content, the reference content comprising clinical guidelines, by repeatedly training a machine learning module, hosted by machine learning system, based on new incoming data, the machine learning module configured to process fuzzy rules to identify whether a segment from the CDS document satisfies a corresponding segment from the reference content comprising clinical guidelines, wherein improving the machine learning system accuracy by training the machine learning module comprises repeatedly:

collecting positive and negative cases from CDS documents, training the machine learning module using the collected positive and negative cases from CDS documents, receiving at the machine learning system a clinical decision support document from a medical service provider system;

accessing, by the machine learning system, reference content corresponding at least in part to the clinical decision support document;

identifying and extracting medical intervention content from the clinical decision support document using the machine learning system;

segmenting, by the machine learning system, at least a portion of the extracted medical intervention content into a first plurality of segments including at least a first segment, comprising a first set of text, and a second segment comprising a second set of text;

determining, using the machine learning module, if the first segment corresponds to at least a first item included in the reference content, the first item comprising a third set of text comprising terminology not present in the first and second sets of text;

determining, using the machine learning module, if a second item included in the reference content corresponds to at least one of the first plurality of segments;

at least partly in response to:

determining that the first segment, comprising the first set of text, corresponds to the first item included in the reference content, the first item comprising the third set of text, and determining that the second item included in the reference content does not correspond to at least one of the first plurality of segments:

dynamically generating a version of the clinical decision support document that includes:

a visual indication that the first segment corresponds to the first item included in the reference content, and a visual indication that the first plurality of segments fails to include at least one segment that corresponds to the second item included in the reference content.

10. The method as defined in claim 9, wherein determining if the first segment corresponds to the first item included in the reference content further comprises:

identifying and tagging phrases that correspond to a medical intervention;

identifying and tagging phrases that correspond to a contraindication;

based on one or more phrase tags, generating a syntactic parse tree comprising verb phrases, noun phrases, determiners, prepositional phrases, nouns, and/or adjectives;

using the syntactic parse tree to identify a main clause.

11. The method as defined in claim 9, the method further comprising:

automatically determining which content features are to be used to determine whether content is to be designated as relevant and matching to the reference content and which content is to be designated as non-relevant and to construct or modify a model accordingly, wherein the features comprise one or more of text length, presence of a medication term, medical intervention language, use of a negation, or context;

using the model to identify and extract medical intervention content from the clinical decision support document; and using feedback with respect to the identification of the medical intervention content to refine the model.

12. The method as defined in claim 9, wherein the clinical decision support document comprises at least one of an order set, a care plan, or clinical support rules.

13. The method as defined in claim 9, wherein the reference content comprises a clinical guideline or a checklist, or both a clinical guideline and a checklist.

14. The method as defined in claim 9, wherein determining if the first segment corresponds to the first item included in the reference content further comprises determining if the first segment comprises a functional synonym using different terminology with respect to the first item included in the reference content.

15. The method as defined in claim 9, wherein determining if the first segment corresponds to the first item included in the reference content further comprises determining if a phrase in the first segment comprises a core concept of the first segment.

16. The method as defined in claim 9, wherein determining if the first segment corresponds to the first item included in the reference content further comprises generating a syntactic parse tree and using the syntactic parse tree to determine if a phrase in the first segment comprises a core concept of the first segment.

17. The method as defined in claim 9, wherein the clinical decision support document comprises field identifiers and corresponding data.

18. The method as defined in claim 9, the method further comprising:

determining whether a first character string in the clinical decision support document corresponds to a network protocol; and at least partly in response to determining that the first character string in the clinical decision support document corresponds to a network protocol, excluding the first character string from the first plurality of segments.

19. The method as defined in claim 9, the method further comprising:

determining whether a first character string in the clinical decision support document exceeds a first number of words or characters; and at least partly in response to determining that the first character string in the clinical decision support document exceeds the first number of words or characters, excluding the first character string from the first plurality of segments.

20. The method as defined in claim 9, wherein segmenting at least a portion of the extracted content into the first plurality of segments further comprises identifying text that is part of a same medically-related intervention.

21. The method as defined in claim 9, wherein segmenting at least a portion of the extracted content into the first plurality of segments further comprises identifying text that is part of a same medical-related intervention based at least in part on one or more of punctuation or indentions.

22. The method as defined in claim 9, wherein identifying and extracting content from the clinical decision support document further comprises:

identifying content related to medicine dosages;

identifying content related to medicine units; and identifying content related to a vital signs measurement.

23. The method as defined in claim 9, wherein the first segment, corresponding to the first item, does not include any words in common with the first item.

24. The method as defined in claim 9, the method further comprising generating an assessment document indicating how many interventions have and have not been verified in two or more categories of intervention.

25. The method as defined in claim 9, wherein generating a version of the clinical decision support document that includes a visual indication that the first segment corresponds to the first item included in the reference content, further comprises using color coding, underlining, bolding, italics, positioning, or font in providing the visual indication that the first segment corresponds to the first item included in the reference content.

* * * * *